(12) United States Patent
Shen et al.

(10) Patent No.: US 8,637,242 B2
(45) Date of Patent: Jan. 28, 2014

(54) INTEGRATED SEQUENCING APPARATUSES AND METHODS OF USE

(71) Applicant: Illumina, Inc., San Diego, CA (US)

(72) Inventors: Min-Jui Richard Shen, Poway, CA (US); Robert C. Kain, San Diego, CA (US); Kenneth M. Kuhn, San Diego, CA (US); AmirAli Hajhossein Talasaz, Menlo Park, CA (US); Arash Jamshidi, Union City, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 13/670,318

(22) Filed: Nov. 6, 2012

(65) Prior Publication Data
US 2013/0116128 A1    May 9, 2013

Related U.S. Application Data

(60) Provisional application No. 61/556,427, filed on Nov. 7, 2011.

(51) Int. Cl.
*C12Q 1/68*    (2006.01)
*B81B 7/00*    (2006.01)
*G01N 27/26*    (2006.01)

(52) U.S. Cl.
USPC .............................. 435/6.1; 204/450; 204/600

(58) Field of Classification Search
None
See application file for complete search history.

(56) References Cited

U.S. PATENT DOCUMENTS

| | | | |
|---|---|---|---|
| 4,997,347 | A | 3/1991 | Roos |
| 5,641,658 | A | 6/1997 | Adams et al. |
| 6,090,592 | A | 7/2000 | Adams et al. |
| 6,172,218 | B1 | 1/2001 | Brenner |
| 6,210,891 | B1 | 4/2001 | Nyren et al. |
| 6,258,568 | B1 | 7/2001 | Nyren |
| 6,274,320 | B1 | 8/2001 | Rothberg et al. |
| 6,306,597 | B1 | 10/2001 | Macevicz |
| 6,465,178 | B2 | 10/2002 | Chappa et al. |
| 6,565,727 | B1 | 5/2003 | Shenderov |
| 6,773,566 | B2 | 8/2004 | Shenderov |
| 6,911,132 | B2 | 6/2005 | Pamula |
| 6,969,488 | B2 | 11/2005 | Bridgham et al. |
| 6,989,234 | B2 | 1/2006 | Kolar et al. |
| 7,057,026 | B2 | 6/2006 | Barnes et al. |

(Continued)

FOREIGN PATENT DOCUMENTS

| | | |
|---|---|---|
| EP | 2016091 | 12/2010 |
| WO | WO 91/06678 | 5/1991 |

(Continued)

OTHER PUBLICATIONS

Darhuber et al., "Microfluidic actuation by modulation of surface stresses," Appl. Phys. Lett. 2003, 82:657-659.*

(Continued)

*Primary Examiner* — Samuel Woolwine
*Assistant Examiner* — Kaijiang Zhang
(74) *Attorney, Agent, or Firm* — John T. Murphy; Illumina, Inc.

(57) ABSTRACT

Provided are methods and apparatuses for performing sequencing using droplet manipulation, for example, via electrowetting-based techniques. Also provided are integrated methods and apparatuses for performing sample preparation and sequencing on the same apparatus. In addition, provided are methods of reducing reagent waste and preloaded consumable cartridges comprising reagents for sample preparation and/or sequencing.

29 Claims, 12 Drawing Sheets

(56) References Cited

U.S. PATENT DOCUMENTS

| | | |
|---|---|---|
| 7,163,612 B2 | 1/2007 | Sterling et al. |
| 7,211,414 B2 | 5/2007 | Hardin et al. |
| 7,268,466 B2 | 9/2007 | Rasmussen |
| 7,315,019 B2 | 1/2008 | Turner et al. |
| 7,329,492 B2 | 2/2008 | Hardin et al. |
| 7,329,860 B2 | 2/2008 | Feng et al. |
| 7,405,281 B2 | 7/2008 | Xu et al. |
| 7,439,014 B2 | 10/2008 | Pamula et al. |
| 7,459,066 B2 | 12/2008 | Broadley et al. |
| 7,556,776 B2 | 7/2009 | Fraden et al. |
| 7,632,388 B2 | 12/2009 | Rikihisa et al. |
| 7,697,187 B2 | 4/2010 | Kato et al. |
| 7,727,723 B2 | 6/2010 | Pollack et al. |
| 7,759,132 B2 | 7/2010 | Pollack et al. |
| 7,815,871 B2 | 10/2010 | Pamula et al. |
| 7,816,121 B2 | 10/2010 | Pollack et al. |
| 7,851,184 B2 | 12/2010 | Pollack et al. |
| 8,040,583 B2 | 10/2011 | Takahashi |
| 8,041,463 B2 | 10/2011 | Pollack et al. |
| 8,048,628 B2 | 11/2011 | Pollack et al. |
| 8,081,389 B2 | 12/2011 | Kirita et al. |
| 8,088,578 B2 | 1/2012 | Hua et al. |
| 8,093,062 B2 | 1/2012 | Winger |
| 8,168,134 B2 | 5/2012 | Lehto |
| 8,187,864 B2 | 5/2012 | Wheeler et al. |
| 8,202,686 B2 | 6/2012 | Pamula et al. |
| 8,221,605 B2 | 7/2012 | Pollack et al. |
| 2002/0115224 A1 | 8/2002 | Rudel et al. |
| 2005/0042648 A1 | 2/2005 | Griffiths et al. |
| 2005/0079510 A1 | 4/2005 | Berka et al. |
| 2005/0100900 A1 | 5/2005 | Kawashima et al. |
| 2005/0130173 A1 | 6/2005 | Leamon et al. |
| 2005/0179746 A1 | 8/2005 | Roux et al. |
| 2006/0188901 A1 | 8/2006 | Barnes et al. |
| 2006/0194331 A1 | 8/2006 | Pamula et al. |
| 2006/0240439 A1 | 10/2006 | Smith et al. |
| 2006/0281109 A1 | 12/2006 | Ost et al. |
| 2007/0128624 A1 | 6/2007 | Gormley et al. |
| 2007/0166705 A1 | 7/2007 | Milton et al. |
| 2007/0242105 A1 | 10/2007 | Srinivasan et al. |
| 2008/0037008 A1 | 2/2008 | Shepard et al. |
| 2008/0108082 A1 | 5/2008 | Rank et al. |
| 2008/0210558 A1 | 9/2008 | Sauter-Starace et al. |
| 2008/0283414 A1 | 11/2008 | Monroe et al. |
| 2009/0026082 A1 | 1/2009 | Rothberg et al. |
| 2009/0127589 A1 | 5/2009 | Rothberg et al. |
| 2010/0111768 A1 | 5/2010 | Banerjee et al. |
| 2010/0137143 A1 | 6/2010 | Rothberg et al. |
| 2010/0236928 A1 | 9/2010 | Srinivasan et al. |
| 2010/0282617 A1 | 11/2010 | Rothberg |
| 2011/0059865 A1 | 3/2011 | Smith et al. |
| 2011/0083964 A1 | 4/2011 | Ulmanella |
| 2011/0104816 A1 | 5/2011 | Pollack et al. |
| 2011/0209998 A1 | 9/2011 | Shenderov |
| 2011/0303542 A1 | 12/2011 | Srinivasan et al. |
| 2011/0311980 A1 | 12/2011 | Pollack et al. |

FOREIGN PATENT DOCUMENTS

| | | |
|---|---|---|
| WO | WO 00/31148 | 6/2000 |
| WO | WO 00/53812 | 9/2000 |
| WO | 00/73655 | 10/2000 |
| WO | 00/69565 | 11/2000 |
| WO | WO 01/01143 | 1/2001 |
| WO | WO 01/62982 | 8/2001 |
| WO | WO 03/014392 | 2/2003 |
| WO | WO 2004/018497 | 3/2004 |
| WO | 2004/029585 | 4/2004 |
| WO | 2004/030820 | 4/2004 |
| WO | WO 2005/010145 | 2/2005 |
| WO | 2005/047696 | 5/2005 |
| WO | 2007012638 | 7/2005 |
| WO | WO 2005/065814 | 7/2005 |
| WO | 2006/013303 | 2/2006 |
| WO | WO 2006/064199 | 6/2006 |
| WO | 2006/070162 | 7/2006 |
| WO | 2006081558 | 8/2006 |
| WO | 2006124458 | 11/2006 |
| WO | 2006124458 A2 | 11/2006 |
| WO | 2006/138543 | 12/2006 |
| WO | 2006134307 | 12/2006 |
| WO | 2007/003720 | 1/2007 |
| WO | WO 2007/010251 | 1/2007 |
| WO | 2007/033990 | 3/2007 |
| WO | 2007048111 | 4/2007 |
| WO | 2007120240 | 10/2007 |
| WO | 2007120240 A2 | 10/2007 |
| WO | 2007123908 | 11/2007 |
| WO | WO 2007/123744 | 11/2007 |
| WO | 2008051310 | 5/2008 |
| WO | 2008055256 | 5/2008 |
| WO | 2008068229 | 6/2008 |
| WO | 2008091848 | 7/2008 |
| WO | 2008098236 | 8/2008 |
| WO | 2008106678 | 9/2008 |
| WO | 2008109664 | 9/2008 |
| WO | 2008112856 | 9/2008 |
| WO | 2008116209 | 9/2008 |
| WO | 2008116221 | 9/2008 |
| WO | 2008118831 | 10/2008 |
| WO | 2008124846 | 10/2008 |
| WO | 2008131420 | 10/2008 |
| WO | 2008131420 A3 | 10/2008 |
| WO | 2008/134153 | 11/2008 |
| WO | 2008134153 | 11/2008 |
| WO | 2009002920 | 12/2008 |
| WO | 2009003184 | 12/2008 |
| WO | 2009011952 | 1/2009 |
| WO | 2009021173 | 2/2009 |
| WO | 2009021233 | 2/2009 |
| WO | 2009026339 | 2/2009 |
| WO | 2009029561 | 3/2009 |
| WO | 2009032863 | 3/2009 |
| WO | 2009052095 | 4/2009 |
| WO | 2009052123 | 4/2009 |
| WO | 2009052321 | 4/2009 |
| WO | 2009052345 | 4/2009 |
| WO | 2009052348 | 4/2009 |
| WO | 2009052354 | 4/2009 |
| WO | 2009076414 | 6/2009 |
| WO | 2009086403 | 7/2009 |
| WO | WO 2009/102688 | 8/2009 |
| WO | 2009111769 | 9/2009 |
| WO | 2009/137415 | 11/2009 |
| WO | 2009/140373 | 11/2009 |
| WO | 2009135205 | 11/2009 |
| WO | 2009137415 | 11/2009 |
| WO | 2009140373 | 11/2009 |
| WO | 2009140671 | 11/2009 |
| WO | 2010004014 | 1/2010 |
| WO | 2010006166 | 1/2010 |
| WO | 2010009463 | 1/2010 |
| WO | 2010019782 | 2/2010 |
| WO | 2010027894 | 3/2010 |
| WO | 2010027894 A3 | 3/2010 |
| WO | 2010/042637 | 4/2010 |
| WO | 2010042637 | 4/2010 |
| WO | WO 2010/062965 | 6/2010 |
| WO | 2010077859 | 7/2010 |
| WO | 2011002957 | 1/2011 |
| WO | 2011020011 | 2/2011 |
| WO | 2011057197 | 5/2011 |
| WO | 2011084703 | 7/2011 |
| WO | 2011106314 | 9/2011 |
| WO | 2011106314 A3 | 9/2011 |
| WO | WO 2011/106314 | 9/2011 |
| WO | 2011/126892 | 10/2011 |
| WO | 2011126892 | 10/2011 |
| WO | 2012/009320 | 1/2012 |
| WO | 2012037308 | 3/2012 |
| WO | 2012068055 | 5/2012 |

(56) References Cited

FOREIGN PATENT DOCUMENTS

| | | |
|---|---|---|
| WO | 2013009927 | 1/2013 |
| WO | 2006127451 | 8/2013 |
| WO | 2008101194 | 8/2013 |

OTHER PUBLICATIONS

Guttenberg et al., "Planar chip device for PCR and hybridization with surface acoustic wave pump," Lab Chip 2005, 5:308-317.*

U.S. Appl. No. 61/657,508, Wayne et al.

Adessi et al., "Solid Phase DNA amplification: characterisation of primer attachement and amplification mechanisms", Nucleic Acids Research 28, 2000, 1-8.

Bentley et al., "Accurate whole human genome sequencing using reversible terminator chemistry", Nature, 456, 2008, 53-59.

Dressman et al., "Transforming single DNA molecules into fluorescent magnetic particles for detection and enumeration of genetic variations", PNAS, 100(15), 2003, 8817-8822.

Fedurco et al., "BTA, a novel reagent for DNA attachment on glass and efficient generation of solid-phase amplified DNA colonies", Nucleic Acids Res. 34(3):e22, 2006.

Giraud et al., "Fluorescence lifetime biosensing with DNA microarrays and a CMOS-SPAD imager", Biomedical Optics Express, 1(5), 2010, 1302-1308.

Korlach et al., "Selective aluminum passivation for targeted immobilization of single DNA polymerase molecules in zero-mode waveguide nanostructures", PNAS, 105(4), 2008, 1176-1181.

Levene et al., "Zero-Made Waveguides for Single-Molecules Analysis at high concentrations", Science 299, 2003, 682-686.

Mitra et al., "In situ localized amplification and contact replication of many individual DNA molecules", Nucleic Acids Research, Oxford University Press, GB vol. 27 No. 24, 1999, p. e34.

Stoppa et al., "A 32×32-Pixel Array with In-Pixel Photon Counting and Arrival Time Measurement in the Analog Domain", IEEE European Solid-State Device Conference (ESSCIRC), Athens, Greece, IEEE, 2009, 204-207.

Bali, et al., "Comparison of Methods for the Analysis of Lysosomal Enzyme Activities in Quality Control Dreid Blood Spot Specimens", 9th Annual World Symposium, Feb. 12-15, 2013, Orlando, Florida, p. S22., Feb. 12, 2013, S22.

Bali, et al., "Comparison of Methods for the Analysis of Lysosomal Enzyme Activities in Quality Control Dried Blood Spot Specimens", International Conference on Inborn Errors of Metabolism & Second National Conference of ISIEM Programme and Abstract Book, Apr. 5-7, 2013, New Delhi, India, pp. 96-97.

Bali, et al., "Digital Microfluidics: A Single Multiplex Platform for Rapid Newborn Screening", International Conference on Inborn Errors of Metabolism & Second National Conference of ISIEM Programme and Abstract Book, Apr. 5-7, 2013, New Delhi, India.

Benton, et al., "Library Preparation Method 1: DNA Library Construction for Illumina SBS Sequencing Platforms using NEBNext Library Preparation Reagents", Application Note, NuGEN Technologies, Inc., 2011, 1-6.

Boles, et al., "Droplet-based Pyrosequencing Using Digital Microfluidics", Analytical Chemistry. Sep. 20, 2011, 83, 8439-8447.

Bottausci, et al., "Fully integrated EWOD Based Bio-Analysis Micro Device", SLAS Lab Automation 2011 Conference, Palm Springs, CA, Jan. 29-Feb. 2, 2011, Abstract No. MP61, p. 77.

Burde, Workshop on TB and HIV Diagnostics in Adult and Pediatric Populations, Silver Spring, MD, retrieved from http://www.blsmeetings.net/TB-HIV-Dx_Wkshop/poster_session.cfm, Jun. 28-30, 2011, Poster Session.

Burton, et al., "Diagnosis of Fabry and Gaucher Diseases from the Pilot Screening of Newborns for Lysosomal Storage Disorder in Illinois", Newborn Screening and Genetic Testing Symposium, San Digeo, CA, Nov. 7-10, 2011, Poster Abstract No. P-08, p. 6, 66.

Chakrabarty, et al., "Automated Design of Microfluidics-Based Biochips: Connecting Biochemistry to Electronics CAD" 2005, 38 pages.

Chakrabarty, et al., "Design Automation Challenges for Microfluidics-Based Biochips", DTIP of MEMS & MOEMS, Montreux, Switzerland, Jun. 1-3, 2005.

Chakrabarty, et al., "Design Automation for Microfluidics-Based Biochips", ACM Journal on Emerging Technologies in Computing Systems, vol. 1, No. 3, Oct. 2005, pp. 186-223.

Chakrabarty, et al., "Design, Testing, and Applications of Digital Microfluidics-Based Biochips", Proceedings of the 18th International Conference on VLSI Design held jointly with 4th International Conference on Embedded Systems Design, IEEE 2005.

Cohen, D., "Automated Multianalyte Screening Tool for Classification of Forensic Samples", The NIJ Conference, Jun. 18-20, 2012.

Cohen, D., "Digital Microfluidic Sample Prep & Bioanalytical Systems", From R&D to Quantitative IVDs, Apr. 24, 2012.

Cohen, D., "Low Cost Sample-to Sequence Device for Human & Pathogen ID", Knowledge Foundation 6th Annual Conference: Integrating Sample Preparation Techniques & Applications, Baltimore, MD, Oct. 18-19, 2012.

Cotten, C et al., "Digital Microfluidics: A novel Platform for Multiplexed Detection of Lysosomal Storage Diseases", http://www.abstracts2view.com/pasall/view.php?nu=PAS08L1 2982, printed May 30, 2013.

Delattre, "Final programme for the 10th CBW Protection Symposium", Kistamässan, Stockholm, Sweden, Jun. 8-11, 2010, 13.

Delattre, et al., "Macro to microfluidics system for biological environmental monitoring", Biosensors and Bioelectronics 36, 2012, 230-235.

Delattre, et al., "Smartdrop: An Integrated System From Sample Preparation to Analysis Using Real-Time PCR", CEA/DRT/LETI-Minatec, Microtechnologies for Biology and Healthcare, 2010, 1 pg.

Delattre, "The 10th International Symposium on Protection against Chemical and Biological warfare Agents", Stockholm, Sweden, Jun. 8-11, 2010, 8 pages.

Delattre, et al., "Towards an Industrial Fabrication Process for Electrowetting Chip Using Standard MEMS Technology", Paper, Twelfth International Conference on Miniaturized Systems for Chemistry and Life Sciences, Oct. 12-16, 2008, 1696-1698 pages.

Delattre, et al., "Towards an Industrial Fabrication Process for Electrowetting Chip Using Standard MEMS Technology", Poster, CEA, Leti-Minatec, Department of Microsystems for Biology and Healthcare, 2008, 2 pages.

Delattre, C., "SMARTDROP: An Integrated System from Sample Preparation to Analysis Using Real-Time PCR", Final Programme for the 10th CBW Protection Symposium, Jun. 8-11, 2010, 13 pages.

Dewey, et al., "Towards a visual modeling approach to designing microelectromechanical system transducers", J. Micromech. Microeng. 9, 1999, 332-340.

Dewey, et al., "Visual modeling and design of microelectromechanical system transducers", Microelectronics Journal 32, 2001, 373-381.

Eckhardt, et al., "Development and Validation of a Single-step Fluorometric Assay for Hunter Syndrome", 2011 Newborn Screening and Genetic Testing Symposium, Nov. 7-10, 2011, 2 pgs.

Emani, et al., "Abstract 14693: Novel Microfluidic Platform for Point of Care Hypercoagulability Panel Testing", 2010, 1 page.

Emani, et al., "Novel microfluidic platform for automated lab-on-chip testing of hypercoagulability panel", Blood Coagulation and Fibrinolysis 23, 2012, 760-768.

Fair, et al., "A Micro-Watt Metal-Insulator-Solution-Transport (MIST) Device for Scalable Digital Bio-Microfluidic Systems", IEE, 2001, 4 pages.

Fair, "Biomedical Applications of Electrowetting Systems", 5th International Electrowetting Meeting, May 31-Jun. 2, 2006, 2 pages.

Fair, et al., "Chemical and Biological Applications of Digital-Microfluidic Devices", IEEE Design & Test of Computers, 2007, 10-24.

Fair, "Digital microfluidics: is a true lab-on-a-chip possible?", Microfluid Nanofluid 3, 2008, 245-281.

Fair, et al., "Electrowetting-Based On-Chip Sample Processing for Integrated Microfluidics", IEEE, May 7, 2010, 32.5.1-32.5.4.

Fair, "Scaling of Digital Microfluidic Devices for Picoliter Applications", The 6th International Electrowetting Meeting, Aug. 20-22, 2008, 2 pages.

(56) References Cited

OTHER PUBLICATIONS

Fouillet, "Bio-protocol integration in digital microfluidic chips", The 6th International Electrowetting Meeting, Aug. 20-22, 2008, 2 pgs.
Fouillet, et al., "Design and Validation of a Complex Generic Fuidic Microprocessor Based on EWOD Droplet for Biological Applications", 9th International Conference on Miniaturized Systems for Chemistry and Life Sciences, Oct. 9-13, 2005, 58-60.
Fouillet, et al., "Digital microfluidic design and optimization of classic and new fluidic functions for lab on a chip systems", Microfluid Nanofluid 4, 2008, 159-165.
Graham, et al., "Development of quality control spots for lysosomal storage disorders under cGMP", 2011 Newborn Screening and genetic testing symposium, Nov. 7-10, 2011, 3 pgs.
Graham, et al., "Fluorometric rwagent kits for screening lysosomal storage disorders: One year stability evaluation and shelf-life recommendations", 2013 Joint Meeting of the Newborn Screening and Genetic Testing Symposium and the International Society for Neonatal Screening, May 5-10, 2013, 3 pgs.
Hua, et al., "Multiplexed Real-Time Polymerase Chain Reaction on a Digital Microfluidic Platform", Analytical Chemistry, 2010, 7 pgs.
Hua, et al., "Rapid Detection of Methicillin-Resistant *Staphylococcus aureus* (MRSA) Using Digital Mircrofluidics", Twelfth International Conference on Miniaturized Systems for Chemistry and Life Sciences, Oct. 12-16, 2008, 3 pgs.
Jary, "Forum 4i", CEA-LETI / Minatec—Department of microTechnologies for Biology and Healthcare, 2009, 3 pgs.
Kleinert, et al., "Digital Microfluidic Platform for Newborn Screening Using Whole Blood in Hospital Settings for Hyperbilirubinemia", 2013 Joint Meeting of the Newborn Screening and Geneic Testing Symposium and the International Society for Neonatal Screening, 2013, 3 pgs.
Kleinert, et al., "Dynamics and Stability of Oil Films During Droplet Transport by Electrowetting", 8th International Meeting on Electrowetting, Jun. 21-23, 2012, 2 pages.
Kleinert, et al., "Dynamics and stability of oil films during droplet transport by electrowetting", 86th ACS Colloid & Surface Science Symposium, Jun. 13, 2012, 2 pages.
Kleinert, et al., "Electric Field-Assisted Convective Assembly of Large-Domain Colloidal Crystals", The 82nd Colloid & Surface Science Symposium, Jun. 15-18, 2008, 3 pages.
Kleinert, et al., "Electric-Field-Assisted Convective Assembly of Colloidal Crystal Coatings", Langmuir 26(12), 2010, 10380-10385.
Kleinert, "Liquid Transport and Colloidal Self Assembly in Thin Wetting Films Driven by Electric Fields", A dissertation submitted to the Graduate Faculty of North Carolina State University in partial fulfillment of the requirements for the degree of Doctor of Philosophy, 2013, 146 pages.
Kleinert, et al., "Symposium MM: Evaporative Self Assembly of Polymers, Nanoparticles, and DNA", MRS, http://www.mrs.org, Apr. 6, 2010, 20 pages.
Malk, et al., "EWOD in coplanar electrode configurations", Proceedings of the ASME 2010 3rd Joint US-European Fluids Engineering Summer Meeting and 8th International Conference on Nanochannels, Microchannels, and Minichannels, Aug. 1-5, 2010, 10 pages.
Marchand, et al., "Organic Synthesis in Soft Wall-Free Microreactors: Real-Time Monitoring of Fluorogenic Reactions", Anal. Chem. 80, 2008, 6051-6055.
Millington, et al., "Digital Microfluidics: A Future Technology in the Newborn Screening Laboratory?", Seminars in Perinatology, vol. 34, No. 2; Digital microfluidics for newborn screening, Apr. 2010, 163-169.
Millington, et al., "Digital Microfluidics: A Novel Platform for Multiplexed Detection of LSDs with Potential for Newborn Screening", 2008 Newborn Screening and Genetics Testing Symposium, Conference Proceedings, 2008, 26 pages.
Millington, et al., "Digital Microfluidics: A Novel Platform for Multiplexing Assays Used in Newborn Screening", Proceedings of the 7th International and Latin American Congress, Oral Presentations; 61 (Supl. 1), 2009, 21-33.
Nuffer, "Sample-To-Sequence Analyzer for Human ID Applications", 23rd International Symposium on Human Identification Poster Abstracts, 2012, 7 pgs.
Paik, "A Digital-Microfluidic Approach to Chip Cooling", IEEE Design & Test of Computers, 2008, 10 pgs.
Paik, et al., "Adaptive Cooling of Integrated Circuits Using Digital Microfluidics", IEEE Transactions on Very Large Scale Integration (VLSI) Systems, vol. 16, No. 4, Apr. 2008, 12 pgs.
Paik, et al., "Adaptive Cooling of Integrated circuits using Digital Microfluidics", Artech House, Inc, 2007, 192 pgs.
Paik, et al., "Adaptive Cooling of Integrated Circuits Using Digital Microfluids", Artech House, Inc, 2007, 192 pgs.
Paik, "Adaptive hot-spot cooling of integrated circuits using digital microfluidics", ProQuest Dissertations and Theses, 2006, 188 pgs.
Paik, "Adaptive Hot-Spot Cooling of Integrated Circuits Using Digital Microfluidics", Proceedings of IMECE2005 2005 ASME International Mechanical Engineering Congress and Exposition, Nov. 5-11, 2005, 6 pgs.
Paik, et al., "Coplanar Digital Microfluidics Using Standard Printed Circuit Board Processes", 9th International Conference on Miniaturized Systems for Chemistry and Life Sciences, Oct. 9-13, 2005, 3 pgs.
Paik, et al., "Droplet-based hot spot cooling using topless digital microfluidics on a printed circuit board", TIMA Editions / Therminic, 2005, 6 pgs.
Paik, et al., "Electrowetting-based droplet mixers for microfluidic systems", Lab Chip, 2003, 28-33.
Paik, et al., "Programmable Flow-Through Real-Time PCR Using Digital Microfluidics", Eleventh International Conference on Miniaturized Systems for Chemistry and Life Sciences, Oct. 7-11, 2007, 3 pgs.
Paik, et al., "Rapid droplet mixers for digital microfluidic systems", Lab Chip, 2003, 253-259.
Paik, "Rapid Droplet Mixers for Digital Microfluidic Systems", A thesis submitted in partial fulfillment of the requirements for the degree of Master of Science in the Department of Electrical and Computer Engineering in the Graduate School of Duke University, 2002, 94 pgs.
Paik, et al., "Thermal Effects on Droplet Transport in Digitial Microfluidics With Applications to Chip Cooling", Inter Society Conference on Thermal Phenomena, 2004, 6 pgs.
Pamula, "A Digital Microfluidics Platform for Multiplexed Explosive Detection", Electronic Noses & Sensors for the Detection of Explosives, 2004, 10 pgs.
Pamula, et al., "A Droplet-Based Lab-on-chip for colorimetric detection of nitroaromatic explosives", IEEE, 2005, 4 pgs.
Pamula, "CHI Genomic Tools & Technologies Summit", Cambridge Healthcare Institute, Jun. 8-10, 2009, 8 pgs.
Pamula, "Cooling of Integrated Circuits Using Droplet-Based Microfluidics", 13th ACM Great Lakes Symposium, 2003, 4 pgs.
Pamula, "Digital Microfluid Methods in Diagnosis of Neonatal Biochemical Abnormalities", Pediatric Academic Societies, 2010, 3 pgs.
Pamula, "Digital Microfluidic lab-on-a-chip", Digital Microfluidics, Dec. 17, 2009, 22 pgs.
Pamula, et al., "Digital Microfluidic lab-on-a-chip for protein crystallization", 5th Protein Structure Initiative "Bottlenecks" Workshop Abstracts, Apr. 13-14, 2006, 2 pgs.
Pamula, et al., "Digital Microfluidic Platform for Multiplexing LSD Assays in Newborn Screening", 7th Annual World Symposium, Feb. 2011, 2 pgs.
Pamula, et al., "Digital Microfluidics Platform for Lab-on-a-Chip Applications", Department of Electrical and Computer Engineering, Duke University, 2002, 1 page.
Pamula, "microfluidic electrowetting-based droplet mixing", Microelectromechanical systems conference, 2001, 11 pgs.
Pamula, et al., "Microfluidic electrowetting-based droplet mixing", Department of Electrical Engineering, Duke University, 2002, 3 pgs.
Pamula, "Rapid LSD Assays on a Multiplex Digital microfluidic Platform for Newborn Screening", 8th World Symposium, 2012, 2 pgs.
Pamula, "Sample-to-sequence diagnostics on a digital microfluidic lab on a chip", Pre-Conference Workshops as part of 4th International Conference on Birth Defects and Disabilities in the Developing World, 2009, 3 pgs.

(56) References Cited

OTHER PUBLICATIONS

Panchapakesan, "Droplet Feedback Mechnanisms on a Digital Microfluidic Platform and Development of Hyperbilirubinemia Panel", A dissertation submitted to the Faculty of the Graduate School of the University at Buffalo, State University of New York in partial fulfillment of the requirements for the degree of Doctor of Philosophy, Jan. 9, 2013, 113 pgs.
Pollack, et al., "Applications of electrowetting-based digital microfluidics in clinical diagnostics", Expert Rev. Mol. Diagn. vol. 11, No. 4, 2011, 393-407.
Pollack, "Continuous sequencing-by-synthesis based on a digital microfluidic platform", National Human Genome Research Institute, Advanced DNA Sequencing Technology Development Meeting, Abstracts & General Information, Mar. 10-11, 2010, 2 pgs.
Pollack, et al., "Electrowetting-based actuation of droplets for integrated microfluidics", Lab Chip, vol. 2, 2002, 96-101.
Pollack, et al., "Electrowetting-based actuation of liquid droplets for microfluidic applications", Applied Physics Letters vol. 77, No. 11, Sep. 11, 2000, 1725-1726.
Pollack, "Electrowetting-based microactuation of droplets for digital microfluidics", An abstract of a dissertation submitted in partial fulfillment of the requirements for the degree of Doctor of Philosophy in the Department of Electrical and Computer Engineering in the Graduate School of Duke University, 2001, 159 pages.
Pollack, et al., "Investigation of Electrowetting-Based Microfluidics for Real-Time PCR Applications", mTAS, 2003, 4 pages.
Pollack, "Lab-on-a-chip platform based on digital microfluidics", the 6th International Electrowetting Meeting, 2008, 2 pgs.
Pollack, et al., "The microfluidics, microarrays and BioMEMS Conference and Exhibition", SmallTalk 2001 Final Conference Program, Abstract, Aug. 27-31, 2001, 10 pages.
Punnamaraju, "Voltage and photo induced effects in droplet-interface-bilayer lipid membranes", A dissertation submitted to the Graduate School of the University of Cincinnati in partial fulfillment of the requirements for the degree of Doctor of Philosophy (Ph.D.) in the School of Electronics and Computing Systems College of Engineering and Applied, Nov. 8, 2011, 160 pages.
Punnamaraju, "Voltage Control of Droplet Interface Bilayer Lipid Membrane Dimensions", Langmuir, vol. 27, No. 2, 2011, 618-626.
Ren, et al., "Automated electrowetting based droplet dispensing with good productivity", 7th international conference on miniaturized chemical and biochemical analysis systems, Oct. 5-9, 2003, 993-996.
Ren, et al., "Automated on-chip droplet dispensing with volume control by electro-wetting actuation and capacitance metering", Sensors and Actuators B 98, 2004, 319-327.
Ren, et al., "Design and testing of an interpolating mixing architecture for electrowetting-based droplet-on-chip chemical dilution", Department of Electrical and Computer Engineering, 2003, 4 pages.
Ren, et al., "Dynamics of electro-wetting droplet transport", Sensors and Actuators B, vol. 87, 2002, 201-206.
Ren, et al., "Micro/nano liter droplet formation and dispensing by capacitance metering and electrowetting actuation", IEEE-NANO, Aug. 28, 2002, 369-372.
Rival, "EWOD Digital Microfluidic Device for Single Cells Sample Preparation and Gene Expression Analysis", Palm Springs Convention Center, Abstract, Poster, 2010, 2 pages.
Rival, et al., "EWOD Digital Microfluidic Device for Single Cells Sample Preparation and Gene Expression Analysis—Arnaud RIVAL", From LabAutopedia, http://www.labautopedia.org/mw/index.php/EWOD_Digital_Microfluidic_Device_for_Sing..., Mar. 8, 2013, 2 pages.
Rival, "Expression de génes de quelques cellules sur puce EWOD", Institut de Recherches en Technologies et Sciences pour le Vivant, 2010, 7 pages.
Rival, "Expression de génes de quelques cellules sur puce EWOD", Institut de Recherches en Technologies et Sciences pour le Vivant, 2010, 7 pgs.
Rival, "Gene expression of few cells on EWOD chip", iRTSV Article, 2010, 2 pages.
Rival, et al., "New insight on droplet dynamics under electrowetting actuation and design tools for speeding up product development", Abstract, Mar. 26, 2012, 1.
Rival, et al., "New insight on droplet dynamics under electrowetting actuation and design tools for speeding up product development", 8th International Meeting on Electrowetting, Jun. 21-23, 2012, 2 pages.
Rival, et al., "Towards Single Cells Gene Expression on EWOD Lab on Chip", ESONN 2008 Poster Session, Aug. 26, 2008, 3 pgs.
Rival, et al., "Towards Single Cells Gene Expression Preparation and Analysis on EWOD Lab on Chip", Advances in Microarray Technology, LOC Europe, poster, 2009, 13.
Rival, et al., "Towards Single Cells Gene Expression Preparation and Analysis on EWOD Lab on Chip", Nanobio Europe Proceedings, poster, 2009, 7.
Rouse, et al., "Digital microfluidics: a novel platform for multiplexing assays used in newborn screening.", 41st Annual Oak Ridge Conference, Abstract, Apr. 16-17, 2009, 1 page.
Rouse, "Digital microfluidies: a novel platform for multiplexing assays used in newborn screening", Poster Abstract, 2009, 3 pages.
Rouse, "DNA Library Construction for Illumina SBS Sequencing Platforms using NEBNext®", Library Preparation Method 1, Application Note M01253v2, 2011, 6 pages.
Sandahl, "Automated multianalyte screening for classification of forensic samples", 23rd International Symposium on Human Identification Poster Abstracts, 2012, 7 pages.
Schell, et al., "Evaluation of a digital microfluidic real-time PCR platform to detect DNA of *Candida albicans* in blood", Eur J Clin Microbiol Infect Dis, 2012, 11 pages.
Shi, "Evaluation of stability of fluorometric reagent kits for screening of lysosomal storage disorders", 2011 Newborn screening and Genetic Testing Symposium, 2011, 86-87.
Sista, et al., "96-Immunoassay Digital Microfluidic Multiwell Plate", Twelfth International Conference on Miniaturized Systems for Chemistry and Life Sciences, Oct. 12-16, 2008, 447-449.
Sista, "Development of a digital microfluidic assays for glactosemia and biotindase deficiency in newborn dried blood samples", 2013 Joint Meeting of the Newborn Screening and Genetic Testing Symposium and the International Society for Neonatal Screening, May 5-10, 2013, 106, 3 pages.
Sista, "Development of a digital microfluidic lab-on-a-chip automated immunoassay with magnetically responsive beads", A Dissertation submitted to the Department of Chemical Engineering in partial fulfillment of the Requirements for the degree of Doctor of Philosophy, 2007, 127 pages.
Sista, et al., "Development of a digital microfluidic platform for point of care testing", Lab Chip, vol. 8, 2008, 2091-2104.
Sista, et al., "Digital Microfluidic Platform for Multiplexing Enzyme Assays: Implications for Lysosomal Storage Disease Screening in Newborns", Clinical Chemistry 57:10 Pediatric Clinical Chemistry, 2011, 1-8.
Sista, et al., "Digital Microfluidic Platform for Multiplexing LSD Assays in Newborn Screening", The 2010 Newborn Screening and Genetic Testing Symposium, May 3-6, 2010, 45.
Sista, et al., "Digital microfluidic platform to consolidate enzymatic assays on dried blood spot samples for rapid newborn screening", 2013 Canadian Newborn and Child Screening Symposium, Apr. 11-12, 2013, 37, 4 pages.
Sista, et al., "Heterogeneous immunoassays using magnetic beads on a digital microfluidic platform", Lab Chip, vol. 8, 2008, 2188-2196.
Sista, et al., "Multiplex newborn screening for Pompe, Fabry, Hunter, Gaucher, and Hurler diseases using a digital microfluidic platform", Clinica Chimica Acta, vol. 424, 2013, 12-18.
Sista, et al., "Performance of a digital microfluidic assay for gaucher and hurler disorders", 2011 Newborn Screening and Genetic Testing Symposium, Nov. 7-10, 2011, 65.
Sista, et al., "Rapid assays for Gaucher and Hurler diseases in dried blood spots using digital microfluidics", Molecular Genetics and Metabolism, vol. 109, 2013, 218-220.
Sista, et al., "Rapid, single-step assay for Hunter syndrome in dried blood spots using digital microfluidics", Clinica Chimica Acta, vol. 412, 2011, 1895-1897.
Srinivasan, "3-D Imaging of Moving Droplets for Microfluidics Using Optical Coherence Tomography", mTAS, 2003, 4 pages.

(56) References Cited

OTHER PUBLICATIONS

Srinivasan, et al., "A digital microfluidic biosensor for multianalyte detection", IEEE, 2003, 327-330.
Srinivasan, "A Digital Microfluidic Lab-On-A-Chip for Clinical Diagnostic Applications", Dissertation submitted in partial fulfillment of the requirements for the degree of Doctor of Philosophy in the Department of Electrical and Computer Engineering in the Graduate School of Duke University, 2005, 136 pages.
Srinivasan, et al., "An integrated digital microfluidic lab-on-a-chip for clinical diagnostics on human physiological fluids", Lab Chip, vol. 4, 2004, 310-315.
Srinivasan, "Commercializing electrowetting-based digital microfluidics: from the lab to a product", 8th International Meeting on Electrowetting, Book of Abstracts, Jun. 21-23, 2012, 2 pages.
Srinivasan, et al., "Digital Microfluidic Lab-on-a-Chip for Protein Crystallization", The 82nd ACS Colloid and Surface Science Symposium, Abstract Book, 2008, 269-321.
Srinivasan, et al., "Droplet-based microfluidic lab-on-a-chip for glucose detection", Analytica Chimica Acta, 507, 2004, 145-150.
Srinivasan, "Electrowetting", Methods in Bioengineering, Biomicrofabrication and Biomicrofluidics, Chapter 5, 2010, 26 pages.
Srinivasan, "Feasibility of a point of care newborn screening platform for hyperbilirubinemia", Poster Abstracts, Fair Winds for the Future, Nov. 7-10, 2011, 68, 2 pages.
Srinivasan, et al., "Low-cost digital microfluidic platform for protein crystallization", NIGMS Workshop: Enabling Technologies for Structural Biology, 2009, 2 pages.
Srinivasan, et al., "Protein Stamping for Maldi Mass Spectrometry Using an Electrowetting-Based Microfluidic Platform", SPIE, Oct. 2004, 7 pages.
Srinivasana, et al., "Digital Microfluidics: A novel platform for multiplexed detection of lysosomal storage diseases for newborn screening", 40th Annual Oak Ridge Conference, Poster Abstracts, 25 pages, Apr. 17-18, 2008.
Su, et al., "Yield Enhancement of Digital Microfluidics-Based Biochips Using Space Redundancy and Local Reconfiguration", IEEE, 2005, 6 pages.
Sudarsan, et al., "Printed circuit technology for fabrication of plastic-based microfluidic devices", Anal. Chem. No. 76, 2004, 3229-3235.
Thwar, "DNA sequencing using digital microfluidics", 41st Annual Oak Ridge Conference, Apr. 16-17, 2009, 1 page.
Thwar, et al., "DNA sequencing using digital microfluidics", 41st Annual Oak Ridge Conference, Apr. 16-17, 2009, 1 page.
Tolun, "A novel fluorometric enzyme analysis method for Hunter syndrome using dried blood spots", Molecular Genetics and Metabolism, 2012, 3 pgs.
Tolun, et al., "Dried blood based enzyme assays for lysosomal storage disorders", 2011 Tokyo meeting on lysosomal storage disease screening, Aug. 2011, 2 pgs.
Wang, "Comparison of enzyme activities for pompe, fabry, and gaucher diseases on CDC's quality control spots between microplate fluorometry, mass spectrometry, and digital microfluidic fluorometry", 2011 Newborn screening and genetic testing symposium, Nov. 2011, 2 pgs.
Wang, et al., "Composable Behavioral Models and Schematic-Based Simulation of Electrokinetic Lab-on-a-Chip Systems", IEEE Transactions on Computer-Aided Design of Integrated Circuits and Systems, Vol. 25, No. R2, Feb. 2006, 16 pgs.
Wang, "Droplet-based micro oscillating-flow PCR chip", J. Micromech. Microeng 5, 2005, 1369-1377.
Wang, "Efficient in-droplet separation of magnetic particles for digital microfluidics", J. Micromech. Microeng 17, 2007, 2148-2156.
Wulff-Burchfield, et al., "Microfluidic platform versus conventional real-time polymerase chain reaction for the detection of Mycoplasma pneumonia in respiratory specimens", Diagnostic Microbiology and Infectious Disease 67, 2010, 22-29.
Xu, et al., "A Cross-Referencing-Based Droplet Manipulation Method for High-Throughput and Pin-Constrained Digital Microfluidic Arrays", EDAA, 2007, 6 pgs.
Xu, et al., "Automated Design of Pin-Constrained Digital Microfluidic Biochips Under Droplet-Interference Constraints", ACMJournal on Emerging Technologies in Computing Systems, vol. 3, No. 3, Article 14, Nov. 2007, 23 pgs.
Xu, et al., "Automated, Accurate, and Inexpensive Solutionpreparation on a Digital Microfluidic Biochip", IEEE, 2008, 4 pgs.
Xu, et al., "Defect-Aware Synthesis of Droplet-Based Microfluidic Biochips", 20th International Conference on VLSI Design (VLSID'07), 2007, 6 pgs.
Xu, et al., "Defect-Tolerant Design and Optimization of a Digital Microfluidic Biochip for Protein Crystallization", IEEE Transactions on Computer-Aided Design of Integrated Circuits and Systems, vol. 29, No. 4, Apr. 2010, 14 pgs.
Xu, et al., "Design and Optimization of a Digital Microfluidic Biochip for Protein Crystallization", IEEE, 2008, 5 pgs.
Xu, et al., "Digital Microfluidic Biochip Design for Protein Crystallization", IEEE, 2007, 4 pgs.
Xu, et al., "Droplet-Trace-Based Array Partitioning and a Pin Assignment Algorithm for the Automated Design of Digital Microfluidic Biochips", Department of Electrical and Computer Engineering Duke University, 2006, 6 pgs.
Xu, et al., "Droplet-Trace-Based Array Partitioning and a Pin Assignment Algorithm for the Automated Design of Digital Microfluidic Biochips", Department of Electrical and Computer Engineering Duke University, Oct. 2006, 6 pgs.
Xu, et al., "Integrated Droplet Routing in the Synthesis of Microfluidic Biochips", Department of Electrical and Computer Engineering Duke University, 2007, 6 pgs.
Xu, et al., "Parallel Scan-Like Test and Multiple-Defect Diagnosis for Digital Microfluidic Biochips", IEEE Transactions on Biomedical Circuits and Systems, vol. 1, No. 2, Jun. 2007, 11 pgs.
Xu, et al., "Parallel Scan-Like Testing and Fault Diagnosis Techniques for Digital Microfluidic Biochips", IEEE European Test Symposium (ETS'07), 2007, 6 pgs.
Yang, et al., "Manipulation of droplets in microfluidic systems", Trends in Analytical Chemistry, vol. 29, No. 2, 2010, 17 pgs.
Yi, et al., "Channel-To-Droplet Extractions for On-Chip Sample Preparation", Solid-State Sensors, Actuators, and Microsystems Workshop, Jun. 4-8, 2006, 4 pgs.
Yi, et al., "Characterization of electrowetting actuation on addressable single-side coplanar electrodes", J. Micromech. Microeng. 16, 2006, 2053-2059.
Yi, et al., "EWOD Actuation With Electrode-Free Cover Plate", The 13th International Conference on Solid-State Sensors, Actuators and Microsystems, Jun. 5-9, 2005, 4 pgs.
Yi, et al., "Geometric surface modification of nozzles for complete transfer of liquid drops", Solid-State sensor, acmator and microsystems workshop, Jun. 6-16, 2004, 4 pgs.
Yi, "Soft Printing of biological liquids for microarrays: concept, principle, fabrication, and demonstration", A dissertation submitted in partial satisfaction of the requirements for the degree Doctor of Philosophy in Mechanical Engineering, 2004, 113 pgs.
Yi, et al., "Soft printing of droplets digitized by electrowetting", the 12th international conference on solid state sensors, actuators and microsystems, Jun. 8-12, 2003, 4 pgs.
Yi, et al., "Soft printing of droplets pre-metered by electrowetting", Sensors and Actuators A 114, 2004, 347-354.
Zeng, et al., "Actuation and Control of Droplets by Using Electrowetting-on-Dielectrc", Chin. Phys. Lett. vol. 21, No. 9, 2004, 1851-1854.
Zhao, et al., "Droplet manipulation and microparticle sampling on perforated microfilter membranes", Journal of Micromechanics and Microengineering, vol. 18, 2008, 12 pages.
Zhao, et al., "In-Droplet Particle Separation by Travellingwave Dielectrophoresis (twDEP) and EWOD", Solid-State Sensors, Actuators, and Microsystems Workshop, 181-184, Jun. 4-8, 2006.

(56) References Cited

OTHER PUBLICATIONS

Zhao, "Micro air bubble manipulation by electrowetting on dielectric (EWOD): transporting, splitting, merging and eliminating of bubbles", Lab on a Chip, vol. 7, 2007, 273-280.

Zhao, et al., "Microparticle Concentration and Separation by Traveling-Wave Dielectrophoresis (twDEP) for Digital Microfluidics", Journal of Microelectromechanical Systems, Vol. 16, No. 6, Dec. 6, 2007, 1472-1481.

Zhao, et al., "Optimization Techniques for the Synchronization of Concurrent Fluidic Operations in Pin-Constrained Digital Microfluidic Biochips", IEEE Transactions on Very Large Scale Integration (VLSI) Systems, vol. 20, No. 6, 2012, 1132-1145.

Zhao, et al., "Synchronization of Concurrently-Implemented Fluidic Operations in Pin-Constrained Digital Microfluidic Biochips", 23rd International Conference on VLSI Design, IEEE Computer Society, 2010, 69-74.

* cited by examiner

INTEGRATED SEQUENCING APPARATUSES AND METHODS OF USE

This application is based on, and claims the benefit of, U.S. Provisional Application No. 61/556,427, filed Nov. 7, 2011, which is incorporated herein by reference in its entirety.

BACKGROUND

There is a general interest in developing devices often referred to as labs-on-a-chip, which allow users to perform a variety of chemical and biological reactions on a single device. Examples of such devices include flow-based microfluidic devices and droplet-based mixers. Droplet-based mixers can employ, for example, electrowetting based-techniques to facilitate the movement of droplets electrically using electrodes to independently control each droplet. Briefly, electrodes are arranged on a surface (often in a patterned array) and covered by a hydrophobic layer. When an electrode is activated the portion of the hydrophobic layer covering that electrode becomes hydrophilic and attracts a droplet. Each electrode can be thought of as a control pad or location that is hydrophobic until electrode activation when the pad becomes hydrophilic and, thus, water or droplet attracting. Through proper arrangement and control of the electrodes, a droplet can be successively transported between adjacent electrodes. The electrodes can be arranged as an array in any desired pattern so as to allow transport of a droplet to any location covered by that array. Droplet-based devices can be used to perform a variety of droplet operations including, but not limited to, dispensing, mixing and transporting droplets. Droplet-based devices have been developed for performing biological assays including immunoassays and nucleic acid amplification.

BRIEF SUMMARY

Provided are methods and apparatuses for performing sequencing using dynamic droplet manipulation, for example, via electrowetting-based techniques. Also provided are integrated methods and apparatuses for performing sample preparation and sequencing on the same apparatus (e.g. for nucleic acids). In addition, provided are methods of reducing reagent waste and preloaded consumable cartridges comprising reagents for sample preparation and/or sequencing.

This disclosure provides an apparatus for manipulating droplets, the apparatus including a substrate having an array of dynamic pads (e.g. electrowetting control pads) for performing droplet operations, a subset of the array of dynamic pads including a hydrophilic patch, wherein the ratio of the area of the hydrophilic patch to the dynamic pad allows the droplet to move from a first dynamic pad including the patch to a second dynamic pad.

Also provided is a method of moving a droplet, including the steps of (a) providing a droplet manipulation apparatus (e.g. an electrowetting droplet apparatus) for performing droplet operations, the droplet manipulation apparatus including a substrate surface having an array of dynamic pads (e.g. electrowetting control pads), wherein a droplet dispensed onto the substrate surface moves along a desired path defined by the dynamic pads, and wherein at least one of the dynamic pads includes a hydrophilic patch; (b) moving a droplet on the substrate surface (e.g. using electrowetting) onto a first dynamic pad including a hydrophilic patch; and (c) moving the droplet from the first dynamic pad to a second dynamic pad.

The disclosure further provides a method of sequencing a nucleic acid molecule, including the steps of (a) providing a droplet manipulation apparatus (e.g. an electrowetting droplet apparatus) for performing droplet operations, the droplet apparatus including a substrate surface having an array of dynamic pads (e.g. electrowetting control pads), wherein a droplet dispensed onto the substrate surface moves along a desired path defined by the dynamic pads, and wherein at least one of the dynamic pads includes a hydrophilic patch; (b) transporting a droplet having one or more nucleic acid molecules to be sequenced to the hydrophilic patch; (c) immobilizing the one or more nucleic acid molecules; and (d) sequencing the one or more nucleic acid molecules.

A nucleic acid sequencing method is provided that includes steps of (a) presenting a plurality of target nucleic acids on a detection surface; (b) providing a collection of reagent droplets, individual droplets in the collection having different sequencing reagents, the collection of droplets having sufficient reagents to complete a cycle of the sequencing reaction; (c) delivering droplets from the collection to the detection surface in a sequential order to complete the cycle of the sequencing reaction for the target nucleic acids, wherein at least a subset of individual droplets in the collection are discretely delivered to the detection surface and discretely removed from the detection surface; and (d) re-using individual droplets in the subset in a subsequent cycle of the sequencing reaction.

This disclosure also provides an integrated sequencing device including (a) complementary metal oxide semiconductor circuitry; (b) a substrate having one or more hydrophilic regions for affixing nucleic acids and hydrophobic regions adjacent to said hydrophilic regions; (c) one or more electrodes inferior to the one or more hydrophilic regions; (d) one or more light sensing units inferior to the electrodes; (e) a filter layer between the electrodes and the light sensing units, and (f) one or more channels superior to the substrate, wherein said electrodes effect a flow of reagents through said channel.

Also provided is a method for sequencing a nucleic acid molecule including the steps of (a) providing: (i) a first integrated sequencing device, and (ii) a second nucleic acid sample preparation device in liquid communication with the integrated sequencing device; (b) preparing a nucleic acid sample for sequencing in the second device, wherein the prepared nucleic acid sample flows from the second device to one or more regions on the first device; (c) affixing nucleic acid molecules to the one or more regions on a substrate of the first device; (d) amplifying the affixed nucleic acid molecules such that a plurality of nucleic acid molecules are formed at the one or more regions, and (e) sequencing the plurality of nucleic acid molecules, wherein said sequencing includes detecting the incorporation of nucleotides into the sequencing reaction.

Further provided is a sequencing system including a unit having reagent reservoirs, a detection surface, and one or more fluidic path connecting the reservoirs to the detection surface, wherein the unit is composed of at least two cartridges that fit together to form the unit, wherein the reagent reservoirs are loaded with a preselected amount of the reagents that are in a storage state, and wherein the unit includes a mechanism for automatically introducing fluids to the reagent reservoirs to place the reagents in an active state.

The details of one or more embodiments are set forth in the accompanying drawings and the description below. Other features, objects, and advantages will be apparent from the description and drawings, and from the claims.

DETAILED DESCRIPTION

Figure 1:
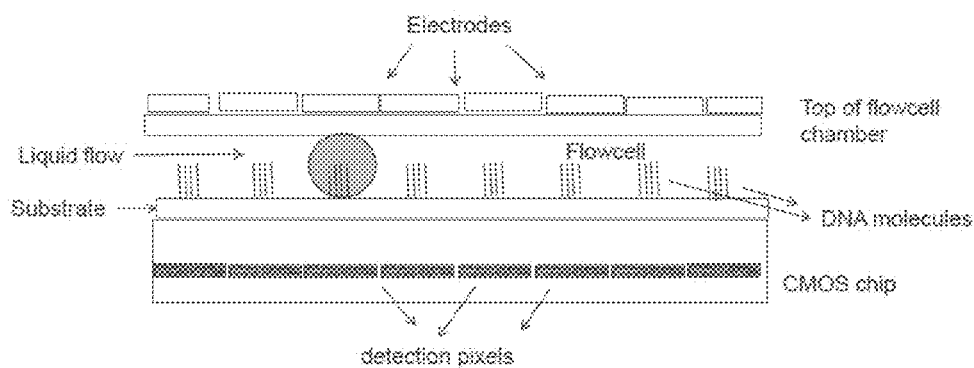
FIG. 1 is a schematic of an exemplary sequencing module of a provided integrated apparatus.

Provided are methods and apparatuses for performing sequencing using electrowetting-based techniques and other droplet manipulation techniques. Also provided are integrated methods and apparatuses for performing sample preparation and sequencing on the same apparatus. In addition, provided are methods of reducing reagent waste and preloaded consumable cartridges comprising reagents for sample preparation and/or sequencing.

Headers are used herein for organizational purposes only and are not necessarily intended to be limiting. It will be understood that one or more embodiments set forth under one header can be used in combination or as an alternative to one or more embodiments set forth under another header.

I. Droplet-Based Sequencing Apparatuses

As described above, there is a general interest in developing devices often referred to as labs-on-a-chip, which allow users to perform a variety of chemical and biological reactions on a single device. Examples of such devices include flow-based microfluidic devices and droplet-based mixers. Droplet-based mixers can employ, for example, electrowetting based-techniques to facilitate the movement of droplets electrically using electrodes to independently control each droplet. However, electrowetting-based devices have been problematic for performing nucleic acid sequencing. For example, it may be necessary to maintain the nucleic acid molecules to be sequenced at a fixed location, while reagents for sequencing the nucleic acid molecules are brought in contact with the nucleic acid molecules. In such methods, nucleic acid molecules are often coupled to a hydrophilic surface. In electrowetting-based techniques, once a droplet is located on a hydrophilic area, the droplet will remain at the hydrophilic area until it becomes hydrophobic (i.e., the electrode is de-activated) and an adjacent area becomes hydrophilic (i.e., an adjacent electrode is activated). A surface containing hydrophilic patches with the nucleic acid molecules to be sequenced can inhibit movement of droplets to and from the location of the patches. This is because the droplet prefers to stay at the hydrophilic area. Thus, to facilitate sequencing using electrowetting-based techniques, a surface is desired that does not inhibit droplet movement to and from the location of the hydrophilic patches with the nucleic acid molecules to be sequenced. Provided is such an apparatus. In such methods and apparatuses, droplets can be used to deposit nucleic acid molecules to be sequenced on a specific location on a surface or substrate followed by delivery of reagents for amplification (e.g., clustering) and/or sequencing to the location of the deposited nucleic acid molecules.

Provided is an apparatus for manipulating droplets, the apparatus including a substrate having an array of dynamic pads (e.g. electrowetting control pads) for performing droplet operations, a subset of the array of dynamic pads including a hydrophilic patch, wherein the ratio of the area of the hydrophilic patch to the dynamic pad allows the droplet to move from a first dynamic pad including the patch to a second dynamic pad.

Also provided is a method of moving a droplet, including the steps of (a) providing a droplet manipulation apparatus (e.g. an electrowetting droplet apparatus) for performing droplet operations, the droplet manipulation apparatus including a substrate surface having an array of dynamic pads (e.g. electrowetting control pads), wherein a droplet dispensed onto the substrate surface moves along a desired path defined by the dynamic pads, and wherein at least one of the dynamic pads includes a hydrophilic patch; (b) moving a droplet on the substrate surface (e.g. using electrowetting) onto a first dynamic pad including a hydrophilic patch; and (c) moving the droplet from the first dynamic pad to a second dynamic pad.

As used throughout, the phrase "electrowetting control pad" refers to a pad or area comprising an electrode covered by a hydrophobic layer. The hydrophobic layer becomes hydrophilic upon activation of the electrowetting control pad. The size of the electrowetting control pad is generally approximately equivalent to the size of the electrode.

As used throughout, the phrase "hydrophilic patch" refers to a composition with hydrophilic properties located at a surface such as on a dynamic pad. The dynamic pad can be an electrowetting control pad. The size of the hydrophilic patch does not inhibit droplet movement to and from the pad. In particular embodiments the hydrophilic patch remains hydrophilic regardless of whether the dynamic pad is activated or not. Taking as an example an electrowetting control pad, a hydrophilic patch located on the pad can be a permanently hydrophilic patch. As such, the patch is always hydrophilic and upon activation of the electrowetting control pad, the portion of the control pad around the permanently hydrophilic patch also becomes hydrophilic to facilitate droplet movement to and from the patch. In an alternative embodiment the hydrophilic patch can be dynamic such that it can be converted from a hydrophilic to hydrophobic state, for example via electrowetting, independently from conversion occurring for the rest of the dynamic pad. For example a dynamic hydrophilic patch can be surrounded by portions of the dynamic pad so that the dynamic pad forms a border or ring around the dynamic hydrophilic patch. The border or ring can be in a hydrophobic state while the dynamic hydrophilic patch is in a hydrophilic state and in this way the border can help contain an aqueous droplet at the patch. The border and the dynamic hydrophilic patch can both be placed into a hydrophobic state to drive aqueous liquid away from the dynamic hydrophilic patch.

Although aspects of the invention are exemplified herein with reference to electrowetting it will be understood that other fluid manipulations can be used as well. Thus, embodiments exemplified herein with regard to electrowetting droplet apparatus are exemplary of similar embodiments using other droplet manipulation apparatus. Similarly embodiments exemplified herein with regard to electrowetting pads can be extended to other dynamic pads.

As used herein, the term "droplet manipulation apparatus" refers to a device for moving a volume of a first fluid within a fill fluid, wherein the first fluid is not miscible with the fill fluid. The first fluid is typically a liquid but can be a gas in some embodiments. The fill fluid can be a liquid or gas. The volume of the first fluid can be partially bounded by the fill fluid. For example, at least 10%, 25%, 50%, 60%, 70%, 80%, or 90% of the surface area of the first fluid can be bounded by the fill fluid. In some embodiments 100% of the surface area of the first fluid can be bounded by the fill fluid. The first fluid can also be partially bounded by a solid-phase surface such that at most 90%, 80%, 70%, 60%, 50%, 25% or 10% of the surface area of the first fluid can be bounded by the fill fluid. In particular embodiments, a droplet can have a volume that is equal to or less than about 100 µL, 50 µL, 10 µL, 1 µL, 500 nL, 100 nL, 50 nL, 10 nL, 1 nL, 500 pL, 100 pL, 50 pL, 10 pL or 1 pL. Exemplary droplet manipulation apparatus are described in U.S. Pat. Nos. 6,911,132; 8,048,628 and 6,773,566; and U.S. Patent Pub. Nos. 2005/0179746 A1; 2010/0236928 and 2011/0311980, each of which is incorporated herein by reference in its entirety. A droplet manipulation apparatus can include a substrate, droplet operations electrodes associated with the substrate, one or more dielectric and/or hydrophobic layers atop the substrate and/or electrodes forming a droplet operations surface, and optionally, a top substrate separated from the droplet operations surface by a gap. One or more electrodes may be provided on the top and/or bottom substrates and/or in the gap.

As used herein the term "dynamic pad" refers to a surface that can be changed from a first state that attracts a droplet to a second state that repels the droplet. Taking aqueous droplets as an example, the first state can be a hydrophilic state and the second state can be a hydrophobic state. In particular embodiments the change in state is reversible. The change in state can be actuated by a physical stimulus. For example the change in state can be electrode mediated, e.g., electrowetting mediated or dielectrophoresis mediated or Coulombic force mediated. Other physical stimuli that may be used in a droplet manipulation apparatus include hydrodynamic fluidic pressure, for example operating on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques or mechanical principles may be employed in droplet manipulation apparatus (or method) of the present disclosure.

Droplets will move through a fill fluid in particular embodiments set forth herein. As used herein, the term "fill fluid" refers to a liquid or gas that is sufficiently immiscible with a droplet to allow the droplet to maintain its volume when in contact with the liquid or gas. The fill liquid may, for example, be a low-viscosity oil, such as silicone oil. Other examples of fill liquids are provided in US Pat. Publ. Nos. 2007/0242105 A1; US 2011/0303542 A1 and 2008/0283414, each of which is incorporated herein by reference in its entirety. A fill fluid can fill the entire gap of a droplet manipulation apparatus or may coat one or more surfaces of the apparatus. Filler fluid may be electrically conductive or non-conductive.

Figure 3:
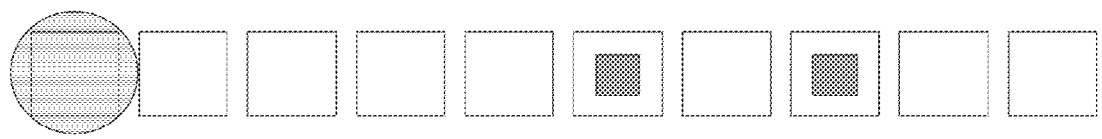
FIG. 3 is an exemplary schematic of the surface of a provided electrowetting droplet-based sequencing apparatus (above view). The boxes are electrowetting control pads. The gray patches represent hydrophilic patches inside an electrowetting control pad. The circle represents a droplet being moved along a series of electrowetting control pads.

As stated above, the dimensions of the hydrophilic patch relative to the pad allow droplet movement, for example by electrowetting-based techniques, to and from the pads comprising the hydrophilic patches. For example, the size of the hydrophilic patch does not inhibit movement of a droplet from a first pad comprising the hydrophilic patch to a second pad. Stated another way, the ratio of the size of the patch to the pad does not inhibit droplet movement or any other droplet operations. Typically, as shown in FIG. 3, the size of the patch will be smaller in size than the pad (i.e., the patch area will be smaller than the pad area). For example, the ratio of the size or area of the pad to the patch can be, 1.25:1, 1.5:1, 1.75:1, 2:1, 2.5:1, 3:1, 3.5:1, 4:1, 4.5:1, or 5:1. The ratio can be any ratio between 1.25:1 and 5:1. Optionally, the ratio can be less than or greater than any of these ratios. In addition to manipulation of hydrophilic patch size, the voltage of the electrode can also be adjusted or optimized to facilitate droplet movement over pads with hydrophilic patches.

Figure 4:
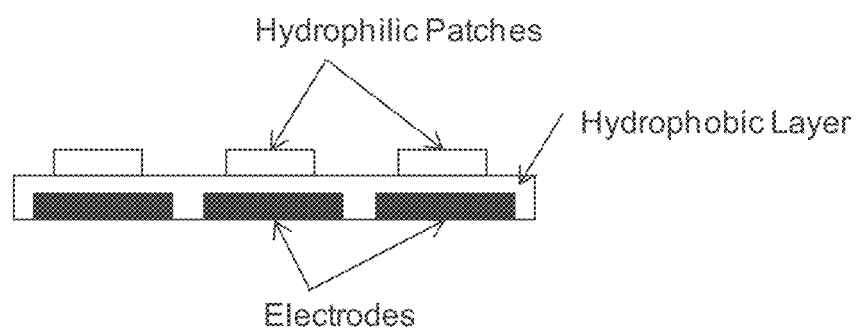
FIG. 4 is an exemplary schematic of hydrophilic patches located on top of the hydrophobic layer of an electrowetting control pad.

The hydrophilic patch can be on the same plane as the hydrophobic layer (e.g., the patch can be on the surface comprising the electrode array) or above or below the hydrophobic layer. For example, as shown in FIG. 4, the hydrophilic patch can be on top of the hydrophobic layer. Optionally, the surface of the electrowetting control pad, or other dynamic pad, can comprise wells comprising the hydrophilic areas. The hydrophilic patch can be comprised of one or more hydrophilic areas being separated from one another by non-hydrophilic areas (e.g., hydrophobic areas). In other words, the patch itself can comprise multiple hydrophilic areas that can be spatially arranged in any desired pattern. For example, the hydrophilic areas can be arranged in a mesh-like pattern each area surrounded by hydrophobic areas. This configuration can be used to average out the interaction between the hydrophobic and hydrophilic areas to facilitate droplet movement. Optionally, the size of the patterned hydrophilic areas can be arranged such that each area corresponds to one nucleic acid molecule to be sequenced (e.g., one cluster).

The hydrophilic patch can include a gel or other microporous material, such as silane-free acrylamide (SFA). Silane-free acrylamide (SFA) polymer may be formed by polymerization of silane free acrylamide and N—(S bromoacetamidylpentyl) acrylamide (BRAPA). Other gels that may be used include without limitation, acrylamide, methacrylamide, hydroxyethyl methacrylate, N-vinyl pyrolidinone or derivatives thereof. Such materials are useful for preparing hydrogels. In some embodiments, the polymerizable material can include two or more different species of compound that form a co-polymer. Exemplary hydrogels and polymerizable materials that may be used to form hydrogels are described, for example, in US Pat. Pub. No. 2011/0059865 A1, which is incorporated herein by reference in its entirety. Other hydrogels include but are not limited to, polyacrylamide polymers formed from acrylamide and an acrylic acid or an acrylic acid containing a vinyl group as described, for example, in WO 00/31148 (which is incorporated herein by reference in its entirety); polyacrylamide polymers formed from monomers that form [2+2] photo-cycloaddition reactions, for example, as described in WO 01/01143 or WO 03/014392 (each of which is incorporated herein by reference in its entirety); or polyacrylamide copolymers described in U.S. Pat. No. 6,465,178, WO 01/62982 or WO 00/53812 (each of which is incorporated herein by reference in its entirety). PAZAM is also useful as set forth in U.S. Ser. No. 61/657,508, which is incorporated herein by reference in its entirety.

The shape of gel pads or pattern of gel pads in a sequencing device of the present disclosure can be varied to facilitate amplification, sequencing or other manipulations of nucleic acids and other molecules set forth herein. For example, in some embodiments a large gel patch can hinder movement of droplets. In such cases, the shape of the gel patches can be altered to occupy an area that is circular, rectangular, square elliptical or other desired shape. The shape can be oriented in a variety of ways with respect to the flow of droplets. For example, a rectangular patch can have its long axis parallel or orthogonal to the direction of droplet flow or the long axis can be at a non-parallel and non-orthogonal angle with respect to the direction of droplet flow. Alternatively or additionally, several small patches can occupy a single location such as a single dynamic pad. This can be useful to provide interstitial regions between patches that are responsive to electrowetting to avoid the gel from hindering movement of droplets across the dynamic pad where the gel patches reside. It can also be useful to create a contoured surface upon which gel patches are placed. For example, gel patches can be located in wells or on posts or other features that cause turbulent passage of droplets. The contours can physically perturb droplet structure to allow mixing of droplet contents with the patch, higher surface area for reaction of droplet contents with contents of the patch, and/or more complete transfer of contents between the droplet and the gel patch.

The hydrophilic patch can comprise a surface capable of indirect or direct nucleic acid molecule attachment. For example, an array of nucleic acids can be present in or on a hydrophobic patch. Suitable compositions for use as hydrophilic patches in the provided methods and apparatuses are described in U.S. Publication No. 2011/0059865, which is incorporated herein by reference in its entirety.

Also provided herein is a method of sequencing a nucleic acid molecule comprising providing electrowetting droplet apparatus for performing droplet operations, the droplet apparatus comprising a substrate surface comprising an array of electrowetting control pads (or other dynamic pads), wherein a droplet dispensed onto the substrate surface moves along a desired path defined by the control pads, and wherein at least one of the pads comprising a hydrophilic patch, transporting a droplet comprising one or more nucleic acid molecules to be sequenced to the hydrophilic patch, immobilizing the one or more nucleic acid molecules, and sequencing the one or more nucleic acid molecules. Optionally, the hydrophilic patch comprises one or more primers. Optionally, the nucleic acid molecules are immobilized by hybridizing to the one or more primers. The nucleic acid molecules can be amplified prior to sequencing.

Figure 5:
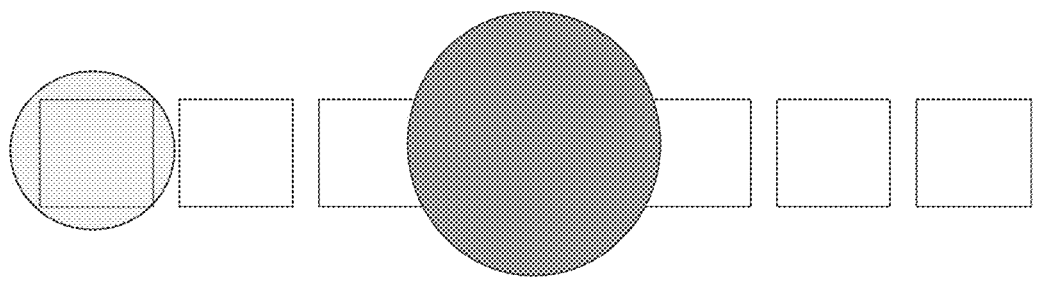
FIG. 5 is an exemplary schematic of droplet movement to a hydrophilic patch containing pad. Droplets (small gray circle) are moved to a droplet containing hydrophilic patch containing pad (large gray circle) as necessary to carry out a desired reaction (e.g., amplification or sequencing round). To exchange reagents, smaller droplets can be separated from the larger droplet and moved away from the hydrophilic patch. A wash droplet may be delivered to the patch after removal of such droplets to dilute residual reagents.

In the provided methods, once nucleic acid molecules in a droplet are deposited onto a hydrophilic patch containing pad, additional droplets can be moved to and from the location of the pad as necessary to carry out one or more of the steps for amplification (or clustering) and sequencing. See FIG. 5. Exemplary reagents and steps used in various amplification techniques are set forth below and in references incorporated below.

II. Integrated Apparatuses—Sample Preparation and Sequencing

In creating an integrated sample preparation/DNA sequencing device, a number of related system modules could be concatenated for insertion into a hardware platform, concatenation to include consumable device configuration, device fluidics, chemistries, and the like. One module could perform, for example, sample preparation and a second module, which could be integrated with the first module, could perform amplification, sequencing and detection methods. Sample preparation can include, for example, one or more of the steps of lysis of cells, extraction of nucleic acids, removal of non-nucleic acid cellular components, fragmentation of nucleic acids, ligation of adapters to nucleic acid fragments (e.g. adapters having universal priming sites) and amplification of adapter ligated nucleic acid fragments (e.g. using universal primers that hybridize to universal priming sites on the adapters). Particularly useful sample preparation methods are those used for commercially available sequencing platforms such as the Genome Analyzer, HiSeq or Miseq platforms available from Illumina (San Diego, Calif.); the SOLiD and Ion Proton platforms available from Life Technologies (Carlsbad, Calif.); or the GS FLX or GS Junior platforms from 454 Life Sciences (a subsidiary of Roche, Branford Conn.). Useful sample preparation techniques are also described in Bentley et al., *Nature* 456:53-59 (2008).

The modules can be located on the same plane (e.g., side-by-side) or located above or below one another. By way of example, a sample preparation module could be located above a sequencing module and fluid containing the prepared sample could flow down into the sequencing module. A device or apparatus as provided herein could comprise two separate but integrated modules wherein fluids are able to flow back and forth between the modules. Alternatively, the device uses the same flow based technique (e.g., electrowetting-based techniques) and the sample preparation and sequencing take place in different areas of the device. For example, the electrowetting droplet-based sequencing apparatus provided herein can also perform nucleic acid library sample preparation. In other words, the sequencing apparatus or module can also prepare the library of nucleic acid molecules for sequencing from a purified DNA sample or another biological sample (e.g., blood or saliva). By way of example, the electrowetting droplet-based sequencing apparatus can comprise areas for nucleic acid sample preparation such as those described in, for example, U.S. Pat. Nos. 6,911,132; 7,815,871; and 7,851,184, each of which is incorporated by reference herein in their entireties. These devices can optionally include all reagents and materials necessary for nucleic acid library preparation. See, for example, WO2011/106314. In such an embodiment, the nucleic acid library preparation can occur in one area of the apparatus and the sequencing can occur in another area on the apparatus. The areas can be two different areas on the same surface. Optionally, the surface is a planar surface.

Thus, a module for sequencing a nucleic acid sample could accept a nucleic acid library preparation from the nucleic acid library preparation module. The sequencing module would provide a substrate for affixing and, optionally, amplifying the nucleic acid library molecules. The sequencing module would include a detector for sequence detection. For example, fluorescence detection of the incorporated nucleotides could be by CMOS pixels underneath the locations of the nucleic acid molecules to be sequenced. Exemplary reagents, procedural steps and detection techniques that can be used in a sequencing process are set forth below and in the references incorporated below. The sequencing data could be output to software for alignment and analysis and finally providing the user with the sequencing results.

An integrated device of modules for library sample preparation and nucleic acid sequencing may be inserted into a hardware unit that would be able to provide for both library preparation and sample sequencing. The sequencing module may be a CMOS chip that has been adapted for sequencing applications. The module can comprise a surface comprising a substrate of hydrophilic regions for nucleic acid attachment and amplification surrounded by hydrophobic regions. For example, dynamic pads having a hydrophilic patch, such as those described above, can be used. Alternatively or additionally, a collection of dynamic pads including some that are in a hydrophilic state while surrounding pads are in a hydrophobic state can form a hydrophilic regions surrounded by a hydrophobic region. The surface for nucleic acid attachment would optionally comprise a plurality of isolated regions such that each isolated region contains a plurality of nucleic acid molecules that is preferably derived from one nucleic acid molecule for sequencing. For example, the hydrophilic region can include a gel. The hydrophilic regions could be smooth, textured, porous, non-porous, etc. The hydrophobic regions are preferably located between the hydrophilic regions. Reagents move across the surface by way of any number of forces. In FIG. 1, electrowetting forces are applied to move reagents between and within a module. FIG. 1 shows separate electrodes located superior to the nucleic acid molecules. Each electrode extends beyond the hydrophilic regions of the nucleic acid molecules into the hydrophobic regions surrounding the hydrophilic regions. The electrodes are in contact with a voltage source (for example, as found in a hardware unit) for driving the electrowetting mechanism for reagent flow. The electrodes are shown superior to or above the nucleic acid molecules; however any arrangement of electrodes is contemplated. For example, electrodes could be positioned inferior to or below the nucleic acid molecules. Inferior positioned electrodes could be transparent, for example to allow fluorescence detection (i.e., from sequencing reaction) by the detection pixels. Further, the electrodes could be positioned in any other manner to manipulate fluids to flow through the module and back and forth between the modules.

Figure 2:
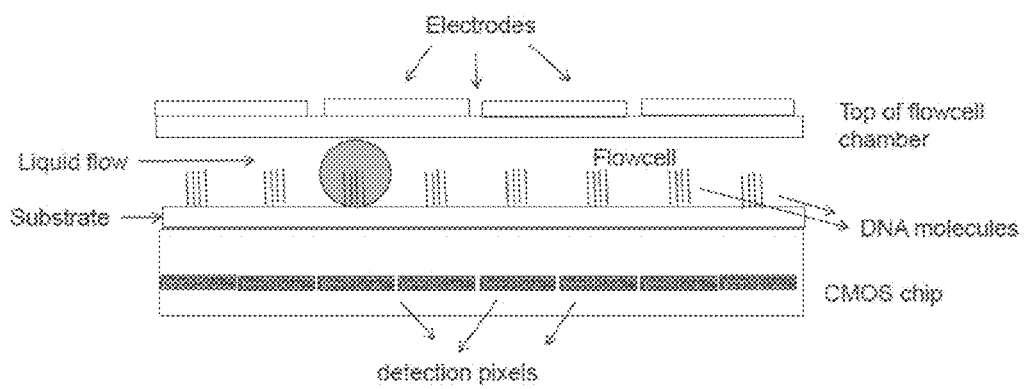
FIG. 2 is a schematic of another exemplary sequencing module of a provided integrated apparatus.

In FIG. 2, the electrodes for providing the electrowetting mechanism are larger electrodes. The number of electrodes could be any number of electrodes as long as those present effect reagent flow across the surface. For movement of reagents by electrowetting, an electric field applied by a voltage source through the electrodes creates a surface tension gradient that causes fluids to move from a ground state electrode towards an energized electrode. As for FIG. 1, the electrodes could be inferior or any other configuration with respect to the nucleic acid molecules as long as fluid flow as desired is maintained. A more detailed discussion of electrowetting is found in, for example, in U.S. Pat. Nos. 6,911,132 and 7,851,184, each of which is incorporated by reference herein in their entireties.

In both FIGS. 1 and 2, fluids could flow in and out of the module from the top, or orthogonal, to the surface substrate. Fluidic movement could also occur planar, or parallel, to the surface substrate. Orthogonal illumination can be applied, for example by one or more lasers found in a hardware unit. Alternatively, illumination can be applied at other angles as long as the excitation wavelength of light is provided to the sequencing reaction for detection of nucleotide incorporation. The nucleotides incorporated during sequencing are detection by CMOS pixels, the data of which is communicated to one or more external systems for data analysis and output. Optionally, one CMOS pixel corresponds to one nucleic acid molecule or plurality of nucleic acid molecules (e.g., a 1:1 ratio).

An integrated device comprising modules for library sample preparation, DNA amplification and sequencing could be used in methods for sequencing one or a number of target DNA molecules. FIGS. 1 and 2 show the use of electrowetting for moving solutions between, and/or within modules. However, forces for moving fluids in the integrated device are not limited to electrowetting microactuator technologies. Other forces for moving reagents could be used in the sequencing module (e.g., the CMOS chip). Other forces include, but are not limited to, temperature gradients, ultrasound (such as acoustic droplet ejection technologies), capillary action, pressure application, vacuum generation, gravity and magnetism.

An integrated device could further include, either within the device or as provided by an external hardware unit, reservoirs for supplying reagents. A preferred device could comprise reservoirs comprising some or all of the reagents necessary for performing sample library preparation, and sequencing collectively within the two modules. As such, means for delivering the reagents as needed for the different reactions and reagent flow could come from a variety of sources. For example, piezoelectric or peristaltic pumps (for example, as described in U.S. Pat. Nos. 7,268,466; 7,459,066; and 4,997,347, respectively, each of which is incorporated by reference herein in its entirety) located in the integrated device or in the hardware unit could be in contact with reagent reservoirs on the modules for effecting fluid movement in combination or concert with electrowetting and/or other fluid movement forces. Further, electroosmotic pumps (for example, as described in WO2009/102688 and WO2010/

062965, each of which is incorporated by reference herein in their entireties) could be incorporated into reagent flow channels for directing fluid flow for the required reactions.

Nucleic acid library molecules prepared from a nucleic acid library preparation module connected to the sequencing module could flow into the sequencing module. The nucleic acid library molecules would affix to the hydrophilic regions of the substrate or hydrophilic patches and reagents for amplification and/or sequencing could flow over the molecules. Reagents for washing, sequencing, etc. could be applied to the clusters for sequencing methodologies. Suitable DNA library preparation modules include, but are not limited to, for example, U.S. Pat. Nos. 6,911,132; 7,815,871; and 7,851,184, each of which is incorporated by reference herein in their entireties. These devices can include some or all of the reagents and materials necessary for nucleic acid library preparation. See, for example, WO2011/106314, which is incorporated by reference herein in its entirety. As described throughout, the sequencing modules described above can be integrated into such modules or apparatuses in order to carry out nucleic acid library preparation and sequencing in the same device.

III. Reagent Consumption

The problem of wasteful consumption of reagents in nucleic acid sequencing reactions can be solved by (a) presenting a plurality of target nucleic acids on a detection surface; (b) providing a collection of reagent droplets, individual droplets in the collection containing different sequencing reagents, the collection of droplets containing sufficient reagents to complete a cycle of the sequencing reaction; (c) delivering droplets from the collection to the detection surface in a sequential order to complete the cycle of the sequencing reaction for the target nucleic acids, wherein at least a subset of individual droplets in the collection are discretely delivered to the detection surface and discretely removed from the detection surface; and (d) re-using individual droplets in the subset in a subsequent cycle of the sequencing reaction.

The problem of wasteful consumption of reagents in nucleic acid synthesis or amplification reactions can be solved by (a) presenting a plurality of template nucleic acids on a detection surface; (b) providing a collection of reagent droplets, individual droplets in the collection containing different nucleic acid synthesis or amplification reagents, the collection of droplets containing sufficient reagents to complete a cycle of the synthesis or amplification reaction; (c) delivering droplets from the collection to the detection surface in a sequential order to complete the cycle of the synthesis or amplification reaction for the template nucleic acids, wherein at least a subset of individual droplets in the collection are discretely delivered to the detection surface and discretely removed from the detection surface; and (d) re-using individual droplets in the subset in a subsequent cycle of the synthesis or amplification reaction.

As used herein, the term "discretely delivered," when used in reference to droplets, means the droplets separately enter a location such that they remain unconnected to each other as they enter. Similarly, the term "discretely removed," when used in reference to droplets, means the droplets separately exit a location such that they remain unconnected to each other as they exit. Individual droplets can be discretely delivered and removed from a detection surface using a technique that maintains droplet integrity such as an electrowetting technique. Maintaining droplet integrity provides several advantages over techniques that use fluid displacement for reagent delivery. Fluid displacement results in dilution of reagents when the displacing fluid interfaces with the fluid to be displaced. Moreover, components of the displacing fluid are introduced into the fluid being displaced. In contrast, when the integrity of a droplet that contains the reagents is maintained such dilution and contamination can be reduced or avoided. Thus, the reagents in the droplets can be more readily re-used, for example, without having to resort to procedures for concentrating or purifying reagents.

A variety of nucleic acid synthesis, amplification and sequencing protocols are known in the art and can be adapted for use in a droplet-based method or system of the present disclosure. Several exemplary protocols and respective reagents are set forth in further detail elsewhere herein and in references incorporated herein. The reagents can be present in the droplets individually or in various combinations as desired to achieve the steps of a particular sequencing cycle. One or more droplets can be re-used in multiple cycles of an amplification, synthesis or sequencing reaction.

An individual droplet that is re-used in a sequencing reaction can include a reagent that is a catalyst and is accordingly not consumed in the cycle of the sequencing reaction. Exemplary catalysts include, but are not limited to, a polymerase, ligase, ATP sulfurylase, luciferase, apyrase, endonuclease, phosphoesterase (e.g. phosphodiesterase or phosphotriesterase), or the like. An individual droplet can include a reagent that is consumed in the cycle, but the droplet can contain an excess amount of the reagent such that the droplet is not depleted upon completion of one or even several cycles of the sequencing reaction. A droplet that contains a catalyst or an excess amount of a consumable reagent can be re-used once or several times.

Wash droplets can be re-used as well. For example, when a series of wash droplets are used, the later droplets will be 'almost clean' having been exposed to a more dilute concentration of contaminants than the first droplets in the series. The almost clean droplets can be recycled and re-used to reduce the volume of wash solution needed to carry out a particular protocol. This can in turn provide for more compact cartridges and apparatus for amplification, sequencing and other applications.

In particular embodiments, a droplet that has been through one or more cycles of a sequencing reaction can be modified or replaced. For example, a droplet can be modified by addition of reagent(s) to replenish the contents of the droplet or the droplet can be replaced with an entirely new droplet having similar reagent(s). The modified droplet or replacement droplet can then be used for subsequent sequencing cycles.

Different droplets can be modified or replaced independently of each other. In a particular embodiment, droplets carrying different types of reagents can be modified or replaced on different schedules. For example, in a polymerase-based sequencing-by-synthesis reaction, a droplet containing a polymerase may be functional for a larger number of cycles than a droplet containing nucleotides. This may be the case for a polymerase that is robust enough to retain activity for a number of cycles that exceeds the number of cycles at which nucleotides are effectively depleted from one or more nucleotide droplet. Accordingly, a nucleotide droplet can be replaced or modified more often than a polymerase droplet. The situation may of course be reversed, for example, where the polymerase is relatively fickle and a large enough excess of nucleotide is present in the nucleotide droplet that the polymerase droplet effectively loses activity before the nucleotide droplet is depleted. Thus, it may be desirable to replace or modify the polymerase droplet more often than the nucleotide droplet.

A given droplet can be replaced, discarded or modified after at least 1, 2, 3, 4, 5, 6, 7, 8, 9, 10, 15, 20, 30, 40, 50, 60, 70, 80, 90, 100 or more uses. Alternatively or additionally, a droplet can be used no more than 1, 2, 3, 4, 5, 6, 7, 8, 9, 10, 15, 20, 30, 40, 50, 60, 70, 80, 90, or 100 times before it is replaced, discarded or modified.

A device for amplification, synthesis and/or sequencing of a nucleic acid can be configured in a variety of ways to achieve discrete delivery and removal of droplets from a particular zone, such as a detection surface. Devices that use electrowetting techniques are particularly useful, including those that operate as described in U.S. Pat. No. 7,815,871; U.S. Pat. No. 6,911,132 and/or WO 2010/077859 A2, each of which is incorporated herein by reference. Such devices provide a fluidic path that is traversed by discrete droplets driven by the electrowetting phenomenon. The devices, or others that operate on similar principles, can be modified to accommodate a sequencing reaction by placing a detection surface in the fluidic path that is traversed by droplets. The detection surface can include one target nucleic acid or several different target nucleic acids (e.g. an array of different target nucleic acids). A series of different droplets can deliver different reagents to the detection surface in a sequential order to complete a cycle of amplification, synthesis and/or sequencing. The cycle can occur for one or more target nucleic acids (e.g., in an array). The fluidic path can be circular such that one or more of the droplets can make several laps, contacting the detection surface each time around. The path can have other shapes that accommodate droplet re-use such as serpentine, clover leaf, figure-eight, spiral or the like.

In particular embodiments, a detection surface is washed with one or more wash droplets. Typically, the detection surface will be washed between each step of a cycle or between cycles, whether the cycles are part of an amplification, synthesis and/or sequencing reaction. However, if desired, washing can be omitted at any step. Wash droplets can be discretely delivered and removed from a detection surface using a technique that maintains droplet integrity. Alternatively, wash droplets can be delivered and combined prior to being removed. Thus, mixing of wash droplets at the detection surface is possible. The number of wash droplets used can be varied to suit a particular application of the methods. Accordingly, at least 1, 2, 3 4, 5, 10, 15, 20, 25 or more wash droplets can be delivered between any given step in a sequencing cycle or between sequencing cycles.

Exemplary detection surfaces include those that have an optical detector. The detector can be based upon any suitable technology, such as those including a charge coupled device (CCD) or a complementary metal-oxide-semiconductor (CMOS). In particular embodiments a CMOS imager having a single-photon avalanche diode (CMOS-SPAD) can be used, for example, to distinguish fluorophores using fluorescence lifetime imaging (FLIM). Exemplary CMOS based systems that can be used for FLIM are described in US Pat. App. Publ. No. 2008/0037008 A1; Giraud et al., *Biomedical Optics Express* 1: 1302-1308 (2010); or Stoppa et al., *IEEE European Solid-State Device Conference* (*ESSCIRC*), Athens, Greece, IEEE, pp. 204-207 (2009), each of which is incorporated herein by reference in its entirety. Other useful detection devices that can be used include, for example, those described in U.S. Pat. No. 7,329,860 and US Pat. App. Publ. No. 2010/0111768 A1, each of which is incorporated herein by reference in its entirety.

In addition, it will be appreciated that other signal detecting devices as known in the art can be used to detect signals produced in a method set forth herein. For example detectors used to detect pyrophosphate or protons are particularly useful. Pyrophosphate release can be detected using detectors such as those commercially available from 454 Life Sciences (Branford, Conn., a Roche Company) or described in US Pat App. Publ. No. 2005/0244870 A1, which is incorporated herein by reference in its entirety. Exemplary systems for detecting primer extension based on proton release include those that are commercially available from Ion Torrent (Guilford, Conn., a Life Technologies subsidiary) or described in US Pat. App. Publ. Nos. 2009/0026082 A1; 2009/0127589 A1; 2010/0137143 A1; and 2010/0282617 A1, each of which is incorporated herein by reference in its entirety.

The methods and compositions set forth herein are particularly useful for multiplex amplification, synthesis and/or analysis of target nucleic acids. For example, an array of target nucleic acids can be present and detected at a detection surface. As used herein, the term "array," when used in reference to molecules, means a population of different molecules that are attached to one or more solid-phase substrates such that the different molecules can be differentiated from each other according to their relative location. An array can include different molecules that are each located at a different addressable location (e.g. a feature) on a solid-phase substrate. Alternatively, an array can include separate solid-phase substrates each bearing a different molecule, wherein the different probe molecules can be identified according to the locations of the solid-phase substrates on a surface to which the solid-phase substrates are attached or according to the locations of the solid-phase substrates in a liquid such as a fluid stream or series of droplets. The molecules of the array can be, for example, nucleic acid primers, nucleic acid probes, nucleic acid templates or nucleic acid enzymes such as polymerases. In particular embodiments target nucleic acids can be attached to a surface or to a layer (e.g. an acrylamide layer) that is present at the surface. Hydrogels are particularly useful such as those set forth in US Pat. Pub. No. 2011/0059865 A1, which is incorporated herein by reference in its entirety. PAZAM and other gels set forth previously herein are also useful. Alternatively or additionally, an array can be present at a hydrophilic patch on a dynamic pad.

Various protocols can be used to generate an array of target nucleic acid features. For example, the features can be generated by emulsion PCR, or bridge PCR (Mitra & Church *Nucleic Acids Res.* 27, e34 (1999); Dressman et al. *Proc. Natl. Acad. Sci. USA* 100, 8817-8822 (2003); Adessi, C. et al. *Nucleic Acids Res.* 28, e87 (2000); Fedurco et al. *Nucleic Acids Res.* 34, e22 (2006), each of which is incorporated herein by reference in its entirety).

In embodiments using emulsion PCR, an in vitro-constructed, adaptor-flanked shotgun library can be PCR amplified in a water-in-oil emulsion. The PCR is multi-template PCR, because only a single primer pair is used. One of the PCR primers is tethered to the surface (5'-attached) of micron-scale beads that are also included in the reaction. A low template concentration results in most bead-containing compartments having either zero or one template molecule present. In productive emulsion compartments (where both a bead and template molecule is present), PCR amplicons can be captured at the surface of the bead. After breaking the emulsion, beads bearing amplification products can be selectively enriched. Each clonally amplified bead will bear on its surface PCR products corresponding to amplification of a single molecule from the template library. Various embodiments of emulsion PCR methods that are useful are set forth in U.S. Pat. App. Publ. Nos. 2005/0042648 A1; 2005/0079510 A1 and 2005/0130173 A1, and WO 05/010145, each of which is incorporated herein by reference in its entirety.

In embodiments using bridge PCR, also known as cluster formation, an in vitro-constructed adaptor-flanked shotgun library can be PCR amplified using primers coated on the surface of a substrate. The primers are attached at their 5' ends by a flexible linker. Amplification products originating from any given member of the template library remain locally tethered near the point of origin. At the conclusion of the PCR, each clonal cluster contains several copies of a single member of the template library. Various embodiments of bridge PCR methods that are useful are set forth in U.S. Pat. App. Publ. No. 2007/0128624 A1, WO 07/010,251, U.S. Pat. No. 6,090,592 and U.S. Pat. No. 5,641,658, each of which is incorporated herein by reference in its entirety.

The methods set forth herein can make or use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

IV. Preloaded Consumable

The problem of controlling the quality of reagents used in a system for amplification, synthesis and/or sequencing can be solved by providing the sequencing system in a unit that has reagent reservoirs, a detection surface, and fluidic path(s) connecting the reservoirs to the detection surface, wherein the unit is composed of at least two cartridges that fit together to form the unit, wherein the reagent reservoirs are loaded with a preselected amount of the reagents that are in a storage state, and wherein the unit includes a mechanism for automatically introducing fluids to the reagent reservoirs to place the reagents in an active state.

In particular embodiments, the storage state for one or more of the reagents is a dry state, for example achieved by lyophilization, freeze drying, evaporation, crystallization or the like. Dry state storage is particularly useful for enzymes and other proteins and for oligonucleotides. Other reagents can be stored in a dry state as well.

Another useful storage state is a low temperature state. For example, one or more reagents can be frozen. Reagents can be stored at liquid ice temperatures (about 0° C.), at dry ice temperature (about −78° C.), at liquid nitrogen temperature (about −196° C.) or any other convenient temperature. Thus reagents can be stored at a temperature below 25° C., 10° C., 5° C., 1° C., 0° C., −40° C., −80° C. or the like. Reagents can be stored at higher temperatures as well including for example at a temperature above 0° C., 1° C., 5° C., 10° C., 25° C. or higher. Storage temperatures can be in a range between the lower and upper values exemplified above. In particular embodiments, cryopreservatives can be in contact with the reagents. Exemplary cryopreservatives include, but are not limited to glycerol, dimethylsulfoxide, and ethylene glycol.

Reagents can be stored in a liquid state. One or more preservatives can be in contact with the reagents. For example, enzymes and other proteins can be stored in the presence of preservatives that prevent denaturation and/or loss of activity. Exemplary preservatives include cryopreservatives such as those exemplified above, chelating agents such as EDTA or EGTA, reducing agents such as dithiothreitol, detergents etc.

An advantage of using separate cartridges to form a sequencing system is that the cartridges can be stored and/or shipped in different states. For example, a subset of one or more reagents that are stored at cold temperatures can be present in a first cartridge that is stored on wet ice, dry ice or liquid nitrogen, whereas a second subset of reagents that is stored at room temperature can be present in a second cartridge that is kept separate from the cooled cartridge until use.

A mechanism for placing reagents in an active state can be activated upon joining two or more cartridges to form a unit. For example, the joining of cartridges can break a seal that allows liquid to flow from one reservoir to a second reservoir. The second reservoir can contain a dried reagent that is put into a liquid state upon entry of the liquid, thereby placing the reagent in an active state. Alternatively, the second reservoir can contain a reagent in a liquid storage state and introduction of a liquid from the first reservoir can wash, dilute or modify the reagent to place it in an active state.

Optionally, the cartridge can be for use on an electrowetting droplet device. In such an embodiment, the cartridge can contain one or more reagent "reservoirs" or areas in which the reagents are located (e.g., freeze-dried onto the surface). Once the cartridge is loaded onto the device, droplets can be delivered to the one or more reagent reservoirs using, for example, electrowetting-based techniques. This results in re-hydration of the enzymes and/or buffers (e.g., additives and the like). The cartridge can be made for re-use. By way of example, the cartridge can perform a biological assay (e.g., amplification and/or sequencing run) one, two, three, four, five, or ten or more times. One cartridge may contain sufficient reagents to perform one or more sample preparation methods (e.g., extraction and/or amplification) and, optionally, may contain sufficient reagents to perform one or more sequencing runs of a library of nucleic acid molecules. By using a cartridge with the reagents in a storage state, only the reagents needed for a given assay need be rehydrated at any given time. Therefore, a cartridge can be used for sequencing a library of nucleic acid molecules on day 1 and then re-used on a different day to sequence another library of nucleic acid molecules (or re-sequence the same library) on day 2. The cartridge can then be used over a period of time according to how much reagents are stored on the cartridge. For example, the cartridge can be used over a period of 10, 20, 30 or more days until all reagents are consumed.

Any of a variety of sequencing protocols and respective reagents can be used in any method or device set forth herein. Sequencing-by-synthesis (SBS) techniques generally involve the enzymatic extension of a nascent nucleic acid strand through the iterative addition of nucleotides against a template strand. SBS can utilize nucleotide monomers that have a terminator moiety or those that lack any terminator moieties. Methods utilizing monomers having terminators include, for example, those described in WO 04/018497, U.S. Pat. No. 7,057,026, WO 91/106678, WO 07/123,744,U.S. US 2007/0166705, US 2006/0188901, US 2006/0240439, US 2006/0281109, WO 05/065814, US 2005/0100900, WO 06/064199 or WO 07010251, the disclosures of which are incorporated herein by reference in their entireties. Also useful are SBS methods that are commercially available from Illumina, Inc., San Diego Calif.

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate or protons; or the like. The different nucleotides can be distinguishable from each other, or alternatively, the two or more different labels can be indistinguishable under the detection techniques being used. For example, the different nucleotides present in a sequencing reagent can have different labels and they can be distinguished using appropriate optics as exemplified by the sequencing methods developed by Solexa (now Illumina, Inc.). However, it is also possible to use the same label for the two or more different nucleotides present in a sequencing reagent or to use detection optics that do not necessarily distinguish the different labels.

Methods utilizing nucleotide monomers lacking terminators are also useful including, for example, pyrosequencing. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." *Analytical Biochemistry* 242(1), 84-9; Ronaghi, M. (2001) "Pyrosequencing sheds light on DNA sequencing." *Genome Res.* 11(1), 3-11; Ronaghi, M., Uhlen, M. and Nyren, P. (1998) "A sequencing method based on real-time pyrophosphate." *Science* 281(5375), 363; U.S. Pat. No. 6,210,891; U.S. Pat. No. 6,258,568 and U.S. Pat. No. 6,274,320, the disclosures of which are incorporated herein by reference in their entireties). In pyrosequencing, released PPi can be detected by being converted to adenosine triphosphate (ATP) by ATP sulfurylase, and the level of ATP generated is detected via luciferase-produced photons. Droplets can be configured to contain pyrosequencing reagents individually or in combinations as desired. Exemplary droplet compositions are set forth for example in WO 2010/077859 or U.S. Pat. No. 7,815,871, each of which is incorporated herein by reference in its entirety.

Some embodiments can utilize sequencing by ligation techniques. Such techniques utilize DNA ligase to incorporate oligonucleotides. Exemplary SBS systems and methods which can be utilized with the methods and systems described herein are described in U.S. Pat. No. 6,969,488, U.S. Pat. No. 6,172,218, and U.S. Pat. No. 6,306,597, the disclosures of which are incorporated herein by reference in their entireties.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-Labeled nucleotides as described, for example, in U.S. Pat. No. 7,329,492 and U.S. Pat. No. 7,211,414 (each of which is incorporated herein by reference in its entirety) or nucleotide incorporations can be detected with zero-mode waveguides as described, for example, in U.S. Pat. No. 7,315,019 (which is incorporated herein by reference in its entirety) and using fluorescent nucleotide analogs and engineered polymerases as described, for example, in U.S. Pat. No. 7,405,281 and U.S. Patent Application Publication No. 2008/0108082 (each of which is incorporated herein by reference in its entirety). The illumination can be restricted to a zeploliter-scale volume around a surface-tethered polymerase such that incorporation of fluorescently labeled nucleotides can be observed with low background (Levene, M.1. et al. "Zero-mode waveguides for single-molecule analysis at high concentrations." *Science* 299, 682-686 (2003); Lundquist, P. M. et al. "Parallel confocal detection of single molecules in real time." *Opt. Lett.* 33, 1026-1028 (2008); Korlach, J. et al. "Selective aluminum passivation for targeted immobilization of single DNA polymerase molecules in zero-mode waveguide nanostructures." *Proc. Nat'l. Acad. Sci. USA* 105, 1176-1181 (2008), the disclosures of which are incorporated herein by reference in their entireties).

Nucleic acid sequencing methods can be particularly sensitive to contamination when carried out using repetitive or cyclic steps. Contaminants that are introduced in early cycles in a sequencing process can have a permanent effect on the nucleic acid being observed and can thus be detrimental to subsequent cycles. Furthermore, although contaminants may be present at sufficiently low levels at any given cycle that their effects are not observed for early cycles, the repeated exposure to low level contaminants can have a cumulative effect that adversely impacts later cycles. Thus, the read length resulting for a sequencing protocol and in particular the quality of data at later cycles (corresponding to the latter nucleotides of each sequence read) can be reduced to undesirable levels.

This disclosure provides apparatus and methods for reducing or preventing unwanted contamination of reagents in a droplet manipulation apparatus or method. Such contamination can occur in situations where reagents from aqueous droplets are capable of transferring between aqueous droplets and a fill liquid that surrounds the aqueous droplets. Taking as an example a sequencing-by-synthesis (SBS) method that uses reversible terminator nucleotides to ensure addition of only one nucleotide per strand per cycle, contamination of an extension step with deblocking reagent will cause several nucleotides to be added at one or more strands that are being observed. This will cause an error in detection since addition of only one nucleotide was expected and it may be difficult or impossible to determine that multiple nucleotides were added to the strand(s). This error can be carried through subsequent cycles carried out for the strand(s) and may manifest as a phasing artifact.

One approach to avoiding cross contamination in a sequencing protocol is to use a fill fluid that does not support diffusion of contaminants from or to the droplets, under the conditions of the sequencing protocol. Also useful is a fill fluid that does not support diffusion of contaminants from or to a gel or solid-phase support where nucleic acid extension is carried out. For example, dodecane is a particularly useful fill liquid in this regard.

A screen can be carried out to identify reagents and fill fluids that are compatible with respect to avoiding diffusional contamination between droplets and fill fluid. For example, a screening apparatus can include two chambers separated from each other by a passage. The passage can be filled with a particular fill fluid, a first chamber can be filled with a reagent from a step of a sequencing reaction that is prone to fouling by a particular contaminant (e.g. a blocked nucleotide) and the second chamber can be filled with the contaminant (e.g. a deblocking agent for the blocked nucleotide). The reagent can be tested periodically for fouling. One can test different fill fluids, different reagents, or different conditions using this or similar screening apparatus.

In particular embodiments, one or more scavengers can be used to sequester, mop up or inactivate a contaminant. The one or more scavengers can be present in a fill fluid such that any contaminants that diffuse into the fill fluid will not be able to adversely influence a sequencing reaction. Useful scavengers can be tested and identified using the screening apparatus described above. Azide is a useful scavenger that can be added to a fill fluid to prevent unwanted contamination of extension reactions with phosphine deblocking reagent.

One or more scavengers can also be loaded into a wash droplet or attached to a solid surface. One or more wash droplets that contain a scavenger can be passed over a solid phase support (e.g. bead or patch), gel or other location where a sequencing reaction takes place. For example, a scavenger for a deblocking reagent can be delivered via a wash droplet after a deblocking droplet has been removed from the location where the sequencing reaction occurs and prior to delivery of an extension reaction droplet to the reaction location. Thus, the deblocking scavenger can be delivered between sequencing cycles.

One or more scavengers can be present at a pad or reservoir that a droplet comes into contact with prior to the droplet contacting the location where a sequencing reaction occurs. The scavenger can be attached to a solid support or gel such that a contaminant in the droplet remains bound to the support or is inactivated by the support. As such, the contaminant will be inhibited from having an adverse impact when the droplet subsequently contacts the location where the sequencing reaction occurs. For example, an enzyme that is selectively reactive toward deblocked nucleotides (and unreactive with blocked nucleotides) can be tethered at a pad or at a bead to mop up the deblocked nucleotides from a droplet prior to the droplet contacting the location where the sequencing reaction occurs.

Cross contamination can also be reduced or prevented by isolation of the path(s) for one or more different reagent droplet from the path(s) taken by one or more other reagent droplets. In many embodiments all droplets in a droplet-based sample preparation and/or sequencing system are carried through a common fill liquid. In particular embodiments, two or more droplet paths can be quarantined from each other by use of separate cartridges or by use of gaskets within a cartridge. The end result is that the fill fluid that comes into contact with droplets in a first train does not come into contact with droplets in a second train. As such the fill fluid does not serve as a carrier for cross contamination between the two droplet trains.

In some embodiments, cross contamination can be reduced or prevented by flowing fill fluid to remove contaminants from the components of a sequencing reaction. This can be particularly useful in situations where reagents from aqueous droplets are capable of transferring between aqueous droplets and a fill liquid that surrounds the aqueous droplets. Here removal of the fill liquid that contacted droplets used in earlier steps of a sequencing cycle removes contaminants from the presence of droplets used in later steps. Similarly, a gel or solid phase that interacts with aqueous droplets in a sequencing protocol can be exposed to flow of a fill liquid that is immiscible to the aqueous droplets and, as such, any contaminants left behind at the gel or solid phase after the aqueous droplets have departed can be removed. Thus, a fill fluid flow can be used to remove contaminants from an array of nucleic acids. The array can be present, for example, on a collection of beads, at one or more patches present on dynamic pads, at one or more patch(es) present on other surfaces present in a droplet manipulation apparatus, or at solid supports otherwise in fluid communication with a droplet manipulation apparatus.

A flow of fill liquid can be continuous throughout all steps of a sequencing protocol. Alternatively the fluid flow can be discontinuous such that it occurs only during particular steps of a sequencing cycle or only during certain cycles of a sequencing protocol (each "cycle" of a sequencing protocol being composed of one or more fluidic manipulation steps (e.g. droplet delivery steps) that are repeated as a unit, such that two units the fluidic manipulation step(s) comprise two cycles, three units of the fluidic manipulation step(s) comprise three cycles etc.). The aqueous-immiscible fluid can be a counter flow that moves in a net direction that is directly opposite the direction that the droplets move or at an angle with respect to the direction that the droplets move. Alternatively, the aqueous-immiscible fluid can flow in the same direction, either directly or at an angle) as the direction that the droplets travel. Thus, in some embodiments a flow of aqueous-immiscible fluid can form a sheath around a moving droplet train. It may alternatively be desired that the aqueous-immiscible fluid flows in a direction that is transverse to a moving droplet train so that fluid that passes over a droplet in a first portion of the droplet train does not contact droplets from another portion of the droplet train.

Fill fluid can flow under a force that is independent of forces placed on the fluid by droplets moving through the fluid. For example the fluid can flow under a force produced by a pump, vacuum, gravity, capillary action, centrifuge, or mixing device. The rate and direction of flow of fill fluid in an apparatus of the present disclosure can be controlled by siphoning through a flow restrictor.

Although apparatus and methods of invention are exemplified herein in the context of nucleic acid sequencing applications, it will be understood that other analytical applications are also well suited for the apparatus and methods. For example, the apparatus and methods disclosed herein can be used for nucleic acid detection (e.g. single nucleotide polymorphism (SNP) detection, mRNA expression analysis, real time PCR), protein binding analysis (e.g. enzyme linked immunosorbent assay), enzyme activity analysis, chemical or protein library screening and detection of labeled analytes.

EXAMPLE I

Fluidic Transfer Between a Sample Preparation Apparatus and a Sequencing Apparatus This example describes multi-module integrated systems for preparation of nucleic acid samples and sequencing of the prepared sample wherein the modules are conveniently separable. Specifically, each system includes a sample preparation cartridge that is in fluidic communication with a sequencing apparatus. A waste reservoir can be present as a separate cartridge or as a sub-component of one of the sample preparation cartridge or sequencing apparatus.

Figure 6A:
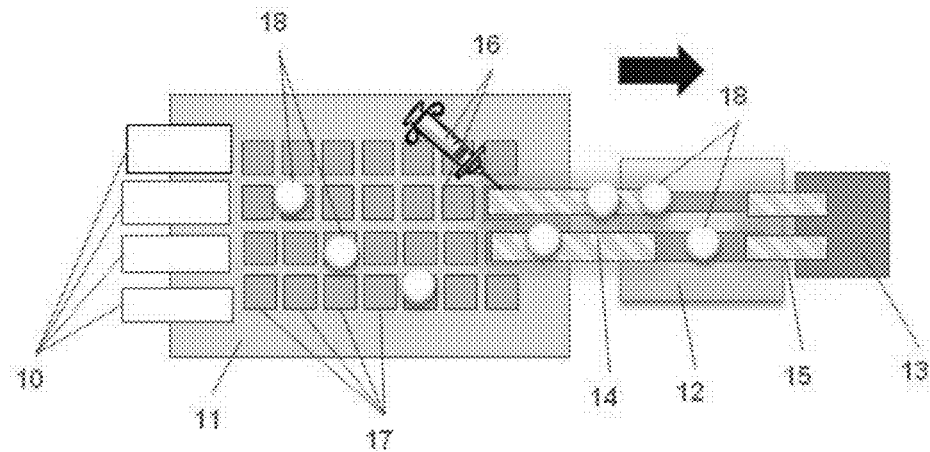
FIGS. 6A and 6B show top and side view, respectively, of an integrated system including a sequencing apparatus fluidically connected to an electrowetting droplet cartridge and waste reservoir.
Figure 6B:
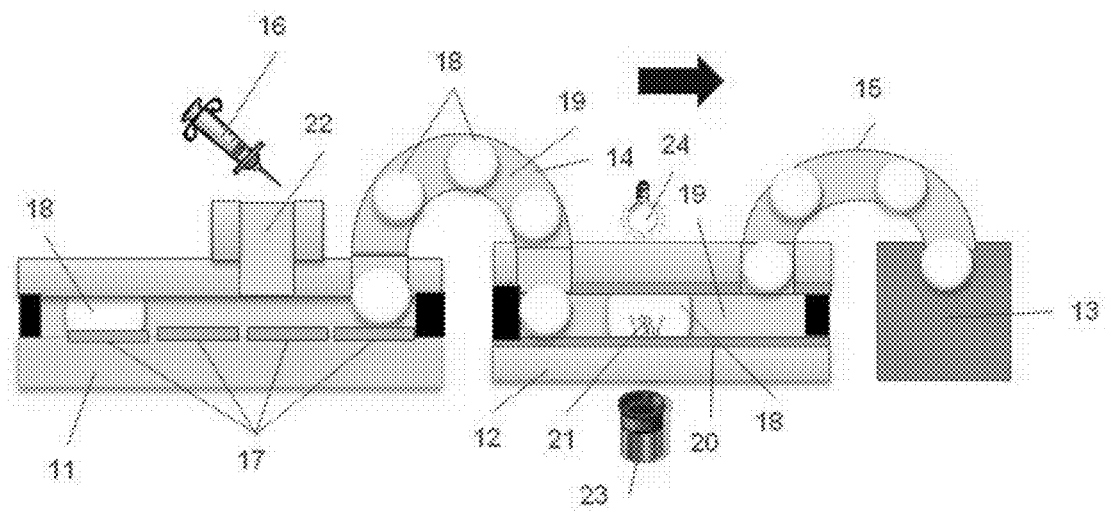

A top plan view of an integrated system including a sequencing apparatus 12 fluidically connected to an electrowetting droplet cartridge 11 and waste reservoir 13 is shown in FIG. 6A. A side view of the integrated system is shown in FIG. 6B. Electrowetting droplet cartridge 11 includes several reservoirs 10 that hold reagents, and optionally samples, for a nucleic acid sample preparation protocol. Reservoirs can also be provided to hold reagents used for amplification of nucleic acids to form clusters on a surface of the sequencing apparatus and reagents used for sequencing-by-synthesis (or other sequencing protocol) at the nucleic acid clusters. The reagents and samples are partitioned into droplets 18 and manipulated by an array of electrowetting control pads 17 to carry out a desired series of steps for preparation of a nucleic acid sample. The droplets travel within a milieu of immiscible oil 19. A manifold 14 connects the sample preparation apparatus 11 to the sequencing apparatus 12. Droplets having nucleic acids samples prepared to the desired state are transferred through manifold 14 under the force of a pump 16. The direction of net fluid flow due to the action of the pump is indicated by the arrow. The pump 16 is shown in an upstream configuration to push liquids to the sequencing apparatus 12. However, it is also feasible to place the pump in a configuration to pull liquids from downstream of the sequencing apparatus 12. The pump will move the droplets and the immiscible oil across manifold 14. Thus, a reservoir of oil 22 is provided to replenish the supply of oil to the system.

Figure 7A:
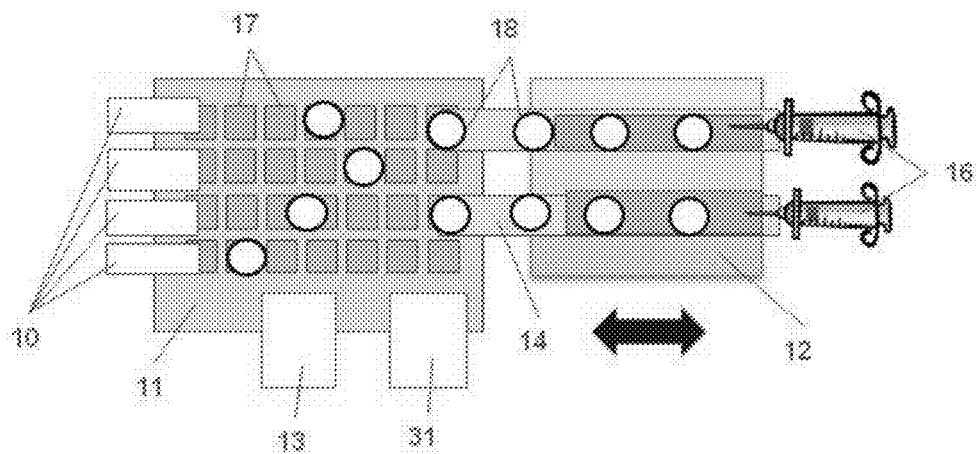
FIGS. 7A and 7B show top and side view, respectively, of an integrated system including a sequencing apparatus fluidically connected to an electrowetting droplet cartridge that is configured for reagent re-use.

The sequencing apparatus 12 can use any of a variety of detection schemes. The sequencing apparatus 12 shown in FIG. 6B is arranged for detection of an immobilized cluster of nucleic acid templates 21 that are attached via a gel layer 20. Sequencing reagents are delivered to the cluster via droplets 18 delivered from the electrowetting droplet cartridge 11. Detection is carried out by exciting fluorophores that have been incorporated at the immobilized cluster (e.g. via polymerase catalyzed incorporation of a fluorescently labeled nucleotide) using a radiation source 24 such as a laser. The fluorescence is detected with a detector 23 such as one that is based on CMOS, CCD or other appropriate camera designs. After passing through the sequencing apparatus the droplets 18 and oil 19 pass via channel 15 into the waste reservoir 13. In this exemplary system the pump pressure is applied in a way to maintain integrity of the droplets 18 in the oil 19 stream as they pass the detector. Detection events can be timed to correspond to the period of time when the cluster of nucleic acids 21 is exposed to a droplet. Alternatively or additionally, pump pressure can be adjusted to slow or pause the passage of droplets through a detection window in order to facilitate extended acquisition times A similar sample preparation and sequencing system is shown in FIG. 7A (top plan view) and FIG. 7B (side view). However, the system differs from that shown in FIGS. 6A and 6B in several ways. First, the electrowetting droplet cartridge 11 is configured to allow re-use of droplets 18. Specifically, pumps 16 are located downstream of both the cartridge 11 and sequencing apparatus 12. The pumps 16 are configured to operate in two directions such that droplets 18 can flow back and forth through a detection window of the sequencing apparatus 12. Thus the contents of a given droplet 18 can contact nucleic acid cluster 21 repeatedly. The system also includes at least one reservoir 31 for containing reagents that are to be recycled. Reservoir 31 provides a location to deposit a droplet's contents after the droplet 18 has been used in a step of a cyclic process carried out on the system (e.g. cluster amplification or sequencing-by-synthesis). The contents can remain in the reservoir 31 while other steps of the methods are carried out and then the contents can be removed for re-use. Droplets 18 can be delivered and removed from the recycle reservoir(s) 31 using the electrowetting control pads 17.

Figure 7B:
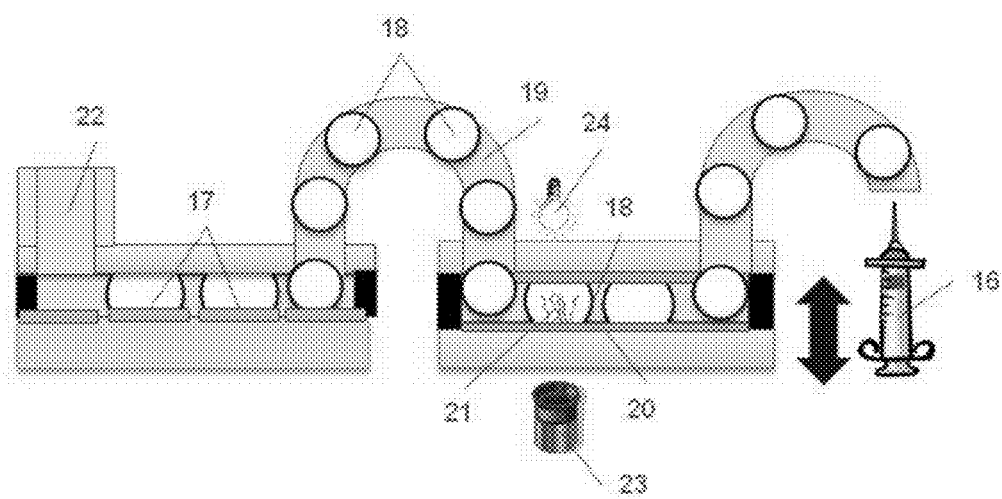

Another feature of the system shown in FIGS. 7A and 7B is that the waste reservoir 13 is provided as a subcomponent of cartridge 11. This configuration allows droplets 18 to be selectively delivered to the waste reservoir 13 by the action of the electrowetting control pads 17. For example, the contents of the recycle reservoir 31 can be purged to the waste reservoir 13 after a desired number of uses or upon indication that the reagents in the recycle reservoir 31 are contaminated or insufficiently potent for their intended use. Similarly, droplets 18 can be removed from the cartridge 11 or from the sequencing apparatus 12 directly to the waste reservoir 13 after a desired number of uses or upon determination that the droplet is contaminated or insufficiently reactive for its intended use.

Figure 8:
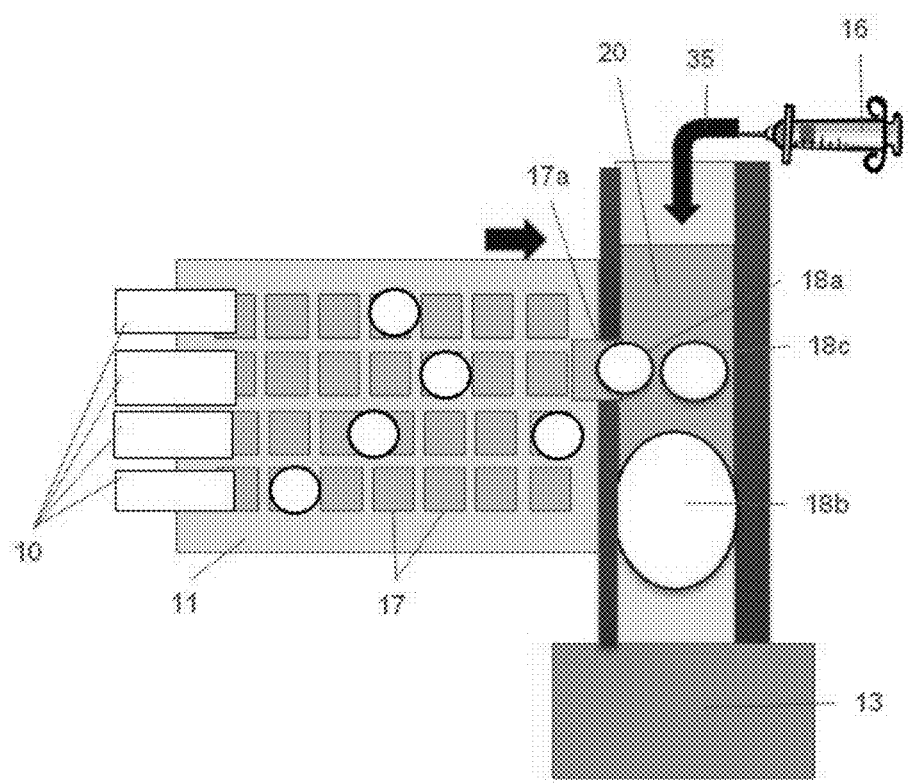
FIG. 8 shows a configuration that uses a dedicated electrowetting pad as a gate between oil in a flow channel and aqueous droplets in an electrowetting droplet cartridge.

The fluidic interface between the electrowetting droplet cartridge 11 and the sequencing apparatus 12 can be configured to control if and when a droplet is transferred. FIG. 8 shows an exemplary configuration that uses a dedicated electrowetting pad 17a as a gate. Here pump 16 is configured to flow oil in a direction 35 that is orthogonal to the direction of egress of droplets 18 from the cartridge 11. So long as gating pad 17a is maintained in a hydrophobic state, droplets 18 will not transfer to the oil stream. However, as shown in FIG. 8, droplet 18a can be transferred to the oil stream by changing gating pad 17a to a hydrophilic state. The droplet 18a then comes into contact with a gel layer 20 where a nucleic acid cluster can reside. Detection can occur at the gel layer 20. Droplets can be discretely maintained by appropriate adjustment of the rate of oil flow with the rate of droplet entry into the oil stream. Droplets can also be accumulated to form a larger volume fluid slug 18b. For example, the flow of oil can be stopped or maintained at a sufficiently slow rate that droplets enter the oil flow and form fluid slug 18b. The system can be configured to detect fluid slug 18b or to detect discrete droplets 18a or 18c. Either way, the fluid in slug 18b, or in discrete droplets 18a and 18c, can be removed to the waste reservoir 13 due to flow of the oil driven by pump 16.

Other configurations for controlling if and when droplets transfer from electrowetting droplet cartridge 11 to sequencing apparatus 12 include use of a valve. For example, a rotary selector valve or binary switching valve can be used. Droplets can be collected in a reservoir area of an electrowetting droplet cartridge. To allow the droplets to coalesce when under force of a pump, the reservoir can include an egress for oil. Alternatively, a series of droplets can be transferred via electrowetting control pads to a reservoir where the droplets coalesce. The valve can be placed to contact the pool of aqueous liquid formed by the accumulated droplets. When the valve is opened, the aqueous liquid can be moved through the valve under applied pressure, vacuum, gravity, capillary action or other force. It is possible to use a combination of valves and gating pads to achieve a desired schedule of droplet transfer to a sequencing apparatus.

Figure 9:
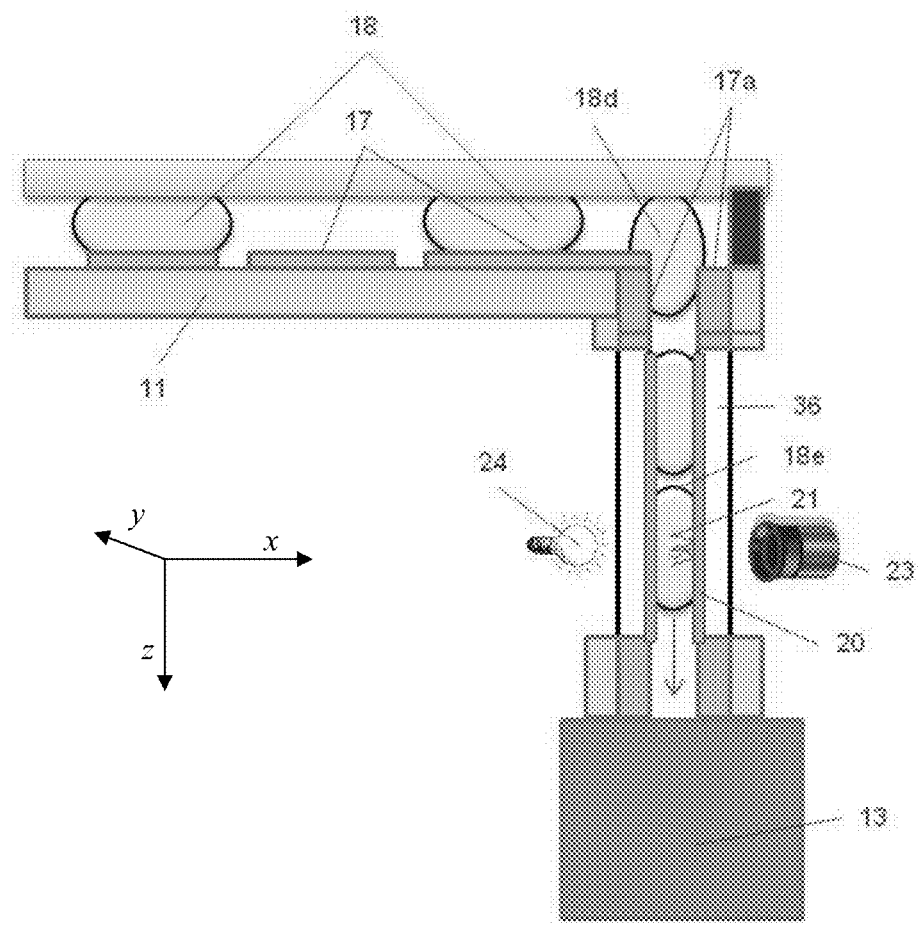
FIG. 9 shows a configuration where droplets are transferred from an electrowetting droplet cartridge to a sequencing apparatus by force of gravity.

FIG. 9 demonstrates a configuration where droplets are transferred from electrowetting droplet cartridge 11 to sequencing apparatus 12 by a force other than pump or vacuum. Here, the droplets 18 are transferred via gravity. Cartridge 11 is shown in a horizontal position such that droplets are transferred in the plane that is orthogonal to gravity (i.e. the x-y plane) by the actuation of electrowetting control pads. The sequencing apparatus is configured with a channel 36 that moves liquids along the z dimension (i.e. parallel to gravitational pull). Gating electrode 17a controls entry of droplets 18 into channel 36. As shown, droplet 18d is entering channel 36 due to gating electrode 17a having been placed in a hydrophilic state. Of course, in the hydrophobic state gating electrode 17a prevents entry of droplets into channel 36. Droplets upon entering channel 36 move by force of gravity to the location where cluster 21 is detected as shown for droplet 18e. After passing through sequencing apparatus 12 the droplets can move to waste reservoir 13.

A configuration that can be used to minimize transfer of oil from an electrowetting droplet cartridge to a sequencing apparatus while allowing droplets to transfer is to use a hydrophilic interface. For example, the surfaces of a sequencing flow cell component and electrowetting cartridge component can be hydrophobic while the entry port between the two components is hydrophilic.

EXAMPLE II

Sample Preparation and Sequencing in a Single Apparatus

This example describes integrated systems for preparation of nucleic acid samples and sequencing of the prepared sample wherein the components form a single module and are practically inseparable. Specifically, each system includes a sample preparation cartridge that includes an integral detection apparatus. It will be understood that various reservoirs and other components can be present as separate subunits.

Figure 10A:
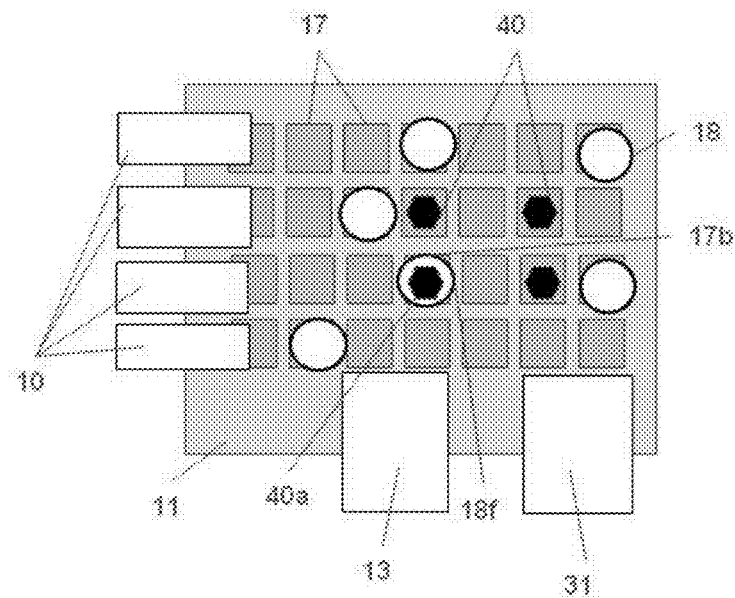
FIGS. 10A and 10B show top and side view, respectively, of an integrated system including an electrowetting droplet cartridge having hydrophilic patches on dynamic pads, wherein the patches are configured to be detected via epifluorescence in a sequencing protocol.
Figure 10B:
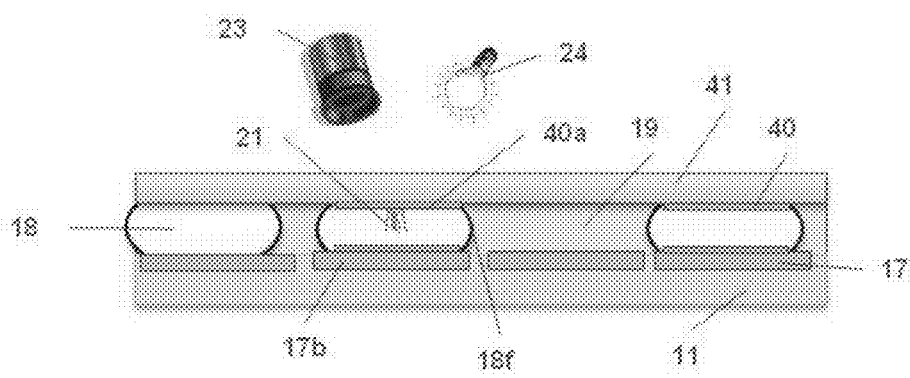

An exemplary device having a solid-phase-attached nucleic acid sample integrated into an electrowetting droplet cartridge 11 is shown in FIG. 10A (top plan view) and FIG. 10B (side view). Various electrowetting control pads 17 in the cartridge 11 include a patch of gel 40 (e.g. silane free acrylamide or PAZAM gel). The patch includes one or more nucleic acid clusters 21, for example, forming an array of clusters. A droplet 18f can be attracted to gel pad 40a due to actuation of electrowetting pad 17b to the hydrophilic state. This can bring reagents for cluster amplification or sequencing-by-synthesis to cluster 21 which is located at gel pad 40a. The cluster 21 can be detected through transparent top plate 41 for example using an epifluorescence detection set up as exemplified in FIG. 10B. The device can include at least one recycle reservoir 31 and can be used for re-use of droplet contents, for example, as set forth in Example 1.

Figure 11:
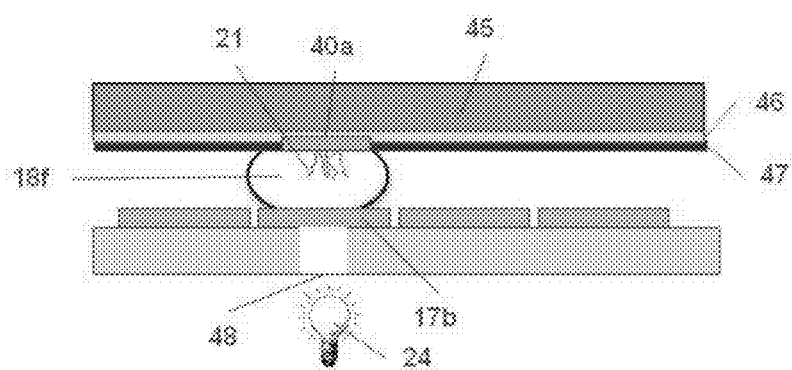
FIG. 11 shows a detector configuration using excitation of a nucleic acid through a dynamic pad that transparent and emission detection with an integrated detector.

FIG. 11 shows an alternative detector configuration from the epifluorescent configuration set forth above. Excitation source 24 is placed to transmit light through an opening 48 in the bottom surface of the cartridge 11 and through electrode 17b. Electrode 17b can be made from a transparent material (e.g. Indium Tin Oxide (ITO)) to facilitate transmission of radiation at a desired wavelength. The radiation excites cluster 21 which is located at gel patch 40a. Gel patch 40a is placed at a window in Teflon surface 47 and atop transparent conducting surface 46 (e.g. surface 46 can be made of ITO). Thus emission light from the cluster 21 (e.g. due to incorporation of a fluorescently labeled nucleotide during SBS) can pass through to CMOS detector 45.

Figure 12A:
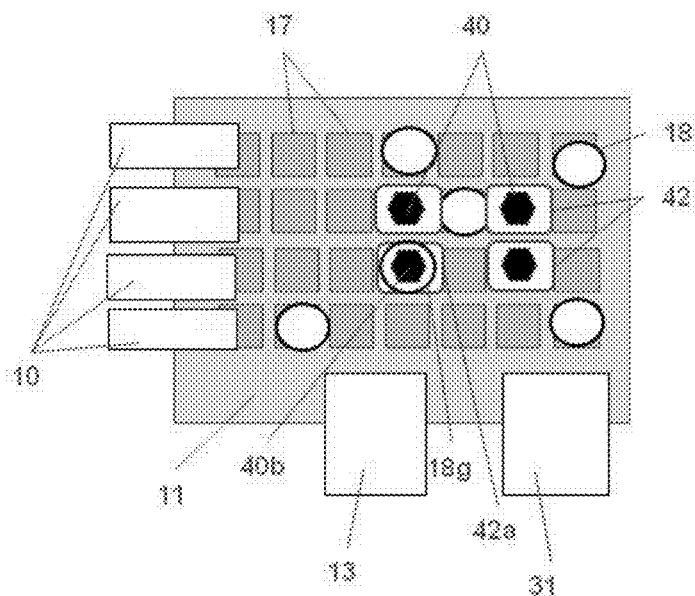
FIGS. 12A and 12B show top and side view, respectively, of an integrated system including an electrowetting droplet cartridge having hydrophilic patches that are located on a non-dynamic surface and are configured to be detected via an integrated detector.
Figure 12B:
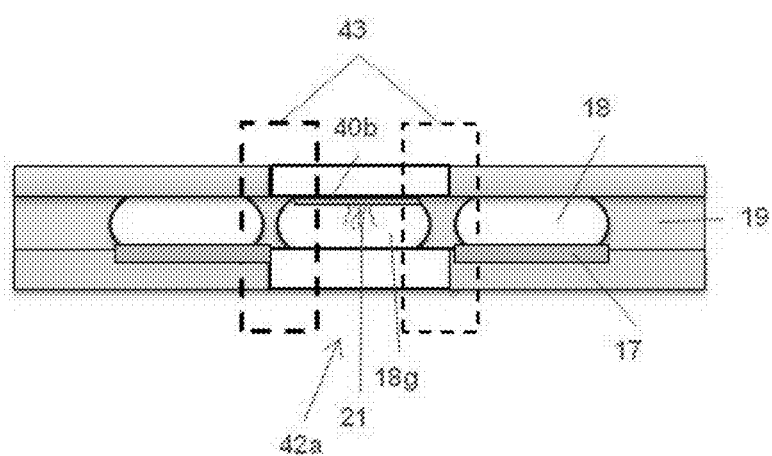

FIG. 12A shows a top plan view and FIG. 12B shows a side view of a device having a detector integrated into an electrowetting droplet cartridge 11. Various locations in the cartridge 11 include a detection device 42 such as a CMOS camera. The locations also include a patch of gel 40 (e.g. silane free acrylamide or PAZAM gel). The patch includes one or more nucleic acid clusters 21, for example, forming an array of clusters. And the clusters are positioned to be detected by detection device 42. As shown in the figures the locations where the detection device 42 resides are contiguous with one or more electrowetting control pads 17 as indicated by the dashed line boxes 43. This juxtaposition allows droplets to be moved to and from the detection location by actuation of the surrounding electrowetting control pads 17. A droplet 18g can be attracted to gel pad 40b in order to bring reagents for cluster amplification or sequencing-by-synthesis to cluster 21 which is located at gel pad 40b. The device can include at least one recycle reservoir 31 and can be used for re-use of droplet contents, for example, as set forth in Example 1.

FIGS. 12A and 12B exemplify an electrowetting droplet cartridge 11 having several individual detectors integrated into the cartridge. In an alternative configuration a large monolithic detector can be integrated into an electrowetting droplet cartridge such that several detection locations (e.g. at positions where locations 42 reside) function as windows that are observed by the monolithic detector.

Figure 13A:
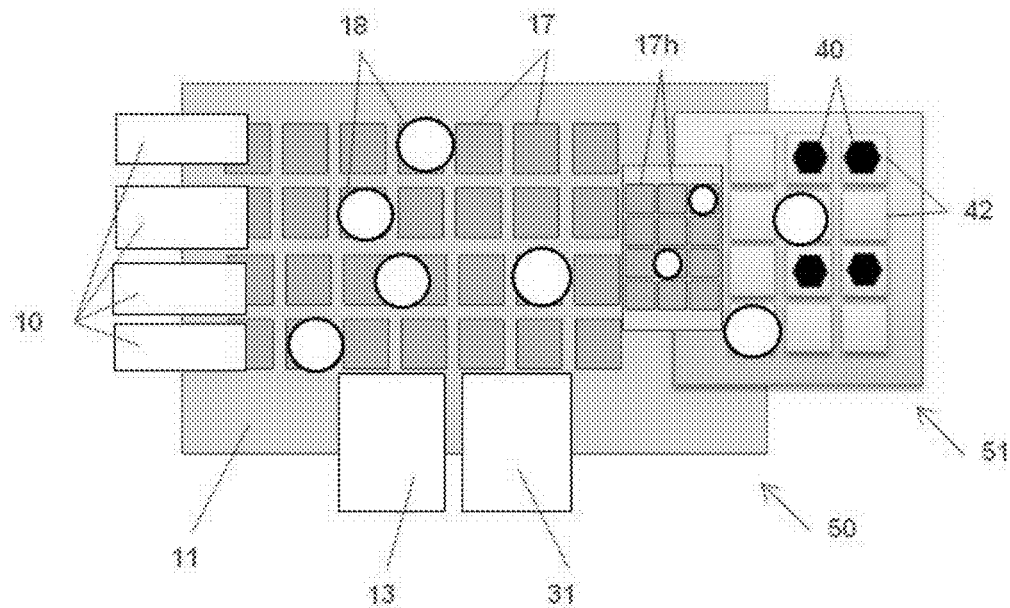
FIGS. 13A and 13B show top and side view, respectively, of a system that utilizes two different regions of electrowetting control pads on opposite sides of a cartridge to transfer droplets from a sample preparation area to a sequencing detection area.
Figure 13B:
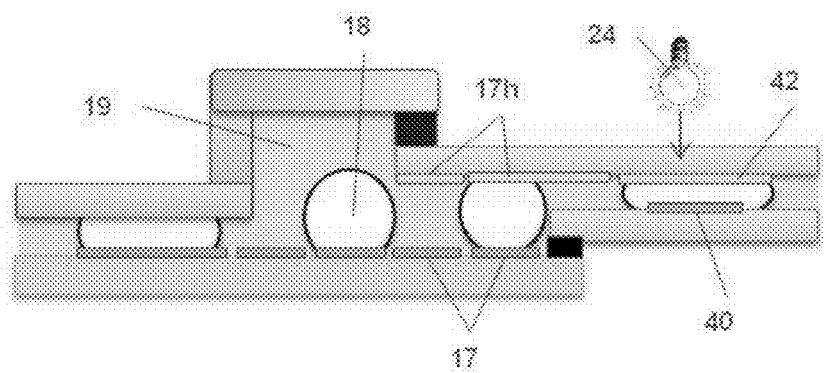

FIG. 13A shows a top plan view and FIG. 13B shows a side view of a system that utilizes two different regions of electrowetting control pads on opposite sides of the cartridge in order to transfer droplets from a sample preparation area 50 of the system to a sequencing detection area 51 of the system. Droplets 18 are moved and manipulated in the sample preparation area of the cartridge using electrowetting control pads 17. The droplets 18 can be transferred from pads 17 to pads 17h. Pads 17h can then move the droplets 18 through the sequencing area of the device. Pads 17 and pads 17h are on opposing faces of a channel in the device. This configuration allows a convenient hand-off of droplets 18 between the two areas. This can be especially convenient when detector 42 is a monolithic detector that observes several regions of the sequencing area. The device can include at least one recycle reservoir 31 and can be used for re-use of droplet contents, for example, as set forth in Example 1.

EXAMPLE III

A Droplet-Based Sequencing Apparatus Configured for Large Volumes and Fast Flow Rates This example demonstrates a droplet-based sequencing device having large volume reservoirs that feed liquids to a network of dynamic pads by gravity driven flow. Flow of liquids from the reservoirs to the network of dynamic pads is controlled by a gating electrode that functions as a valve.

Figure 14:
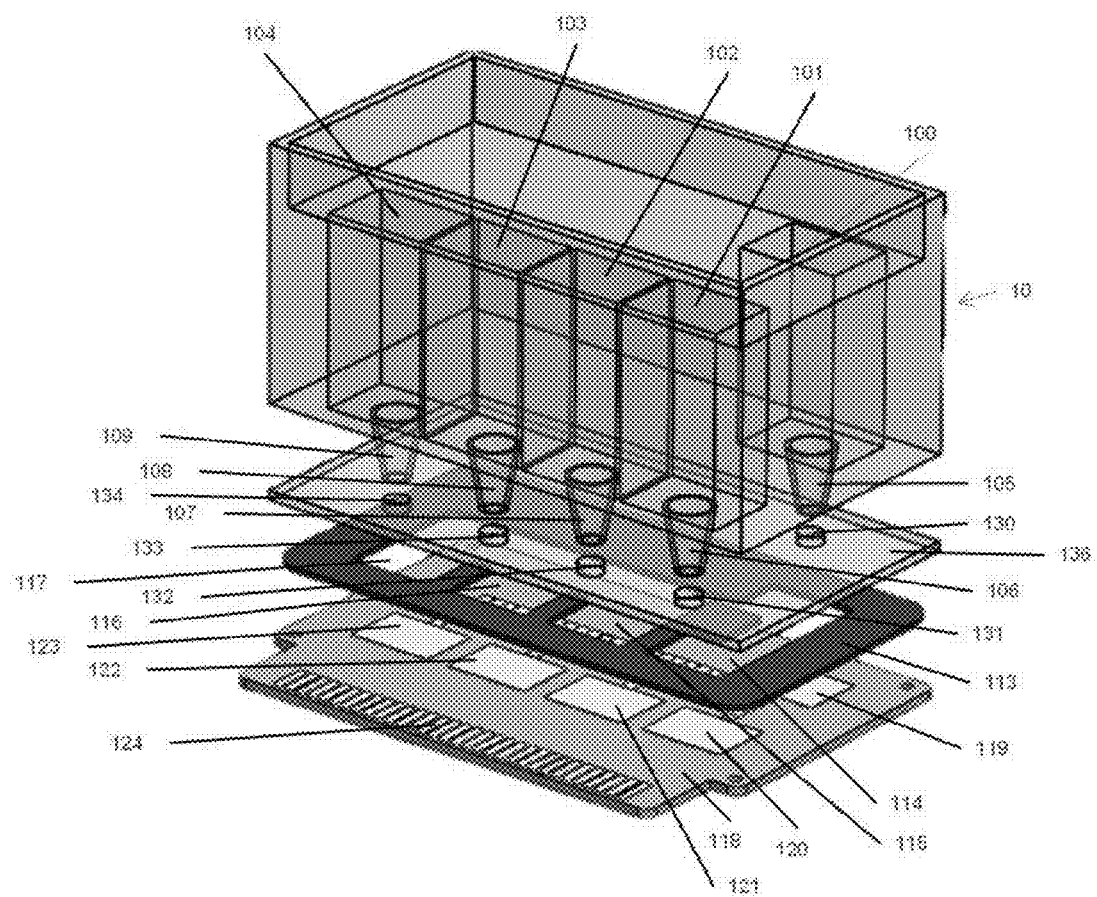
FIG. 14 shows a configuration for gravity driven liquid transfer from reservoirs to electrowetting control pads.

FIG. 14 shows a reservoir subcomponent 10 that is placed into fluid communication with an electrowetting droplet board 118. The reservoir subcomponent 10 includes reservoirs 100 through 104 that have outlets 105 through 109, respectively. The reservoir subcomponent 10 is mated to a top cover 136 such that the reservoir outlets 105 through 109 interface with holes 130 through 134, respectively. Top cover 136 can be an ITO acrylic plate that is laser cut to create holes 130 through 134. Top cover 136 is mated to gasket 113 having openings 114 through 117 that interface with holes 130 through 134 of the top cover 136. The gasket is in turn mated to the electrowetting droplet board 118 so that electrowetting control pads 119 to 123 interface with reservoirs 100 through 104, respectively via the openings 114 through 117 in the gasket 113 and via the holes 130 through 134 in the top cover. A set of electrical contacts 124 are configured to communicate with an external source for activating the electrowetting control pads 119 to 123.

The reservoir subcomponent 10, top cover 136, gasket 113 and electrowetting droplet board 118 are shown in FIG. 14 as an exploded view for clarity. The components can be permanently sandwiched together, for example, by a manufacturer. Alternatively, separate components can be provided by a manufacturer for assembly by an end user. Thus, several of the separate components can include pressure fittings, clips or other convenient connectors for ease of assembly by hand. Once the apparatus is assembled and filled with appropriate liquids, the liquids in the reservoirs 100 through 104 can flow to the electrowetting droplet board 118 under the force of gravity. Gravity driven flow in the device of FIG. 14 can be modulated and controlled by one or more valves such as the exemplary valve described below.

Figure 15:
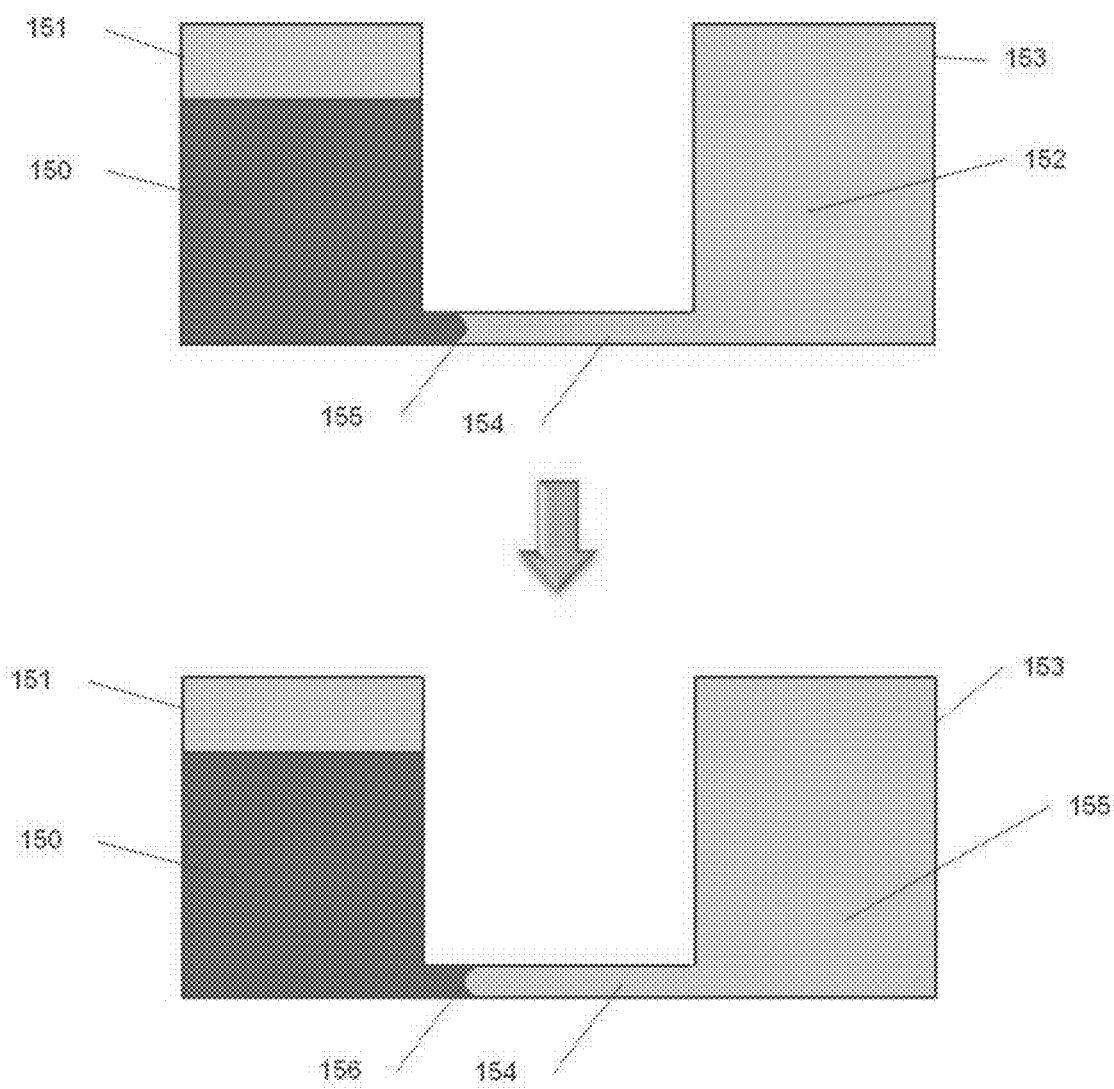
FIG. 15 shows a virtual valve for controlling gravity driven liquid transfer from reservoirs to electrowetting control pads via actuation of a dynamic surface.

FIG. 15 is a diagrammatic representation of a reagent reservoir having a valve mechanism that controls fluid flow using a dynamic surface as a gate. The function of the valve can be exemplified with reference to an electrowetting surface. The upper view shows the valve is in the closed state. An aqueous reagent 150 is present in chamber 151 and a non aqueous fluid 152 that is immiscible with the aqueous reagent (e.g. gas or oil) is present in chamber 153. The aqueous fluid 150 comes into contact with the non-aqueous fluid 152 at passage 154. The passage 154 includes an electrowetting surface that is in a hydrophobic state in the upper view. In this state, the surface pressure asserted on the aqueous fluid 150 is greater than hydraulic pressure resulting from force of gravity on the aqueous fluid 150. As shown in the upper view, the aqueous reagent 150 has a high contact angle due to the hydrophobicity and relatively small cross-sectional dimensions of passage 154. Changing the electrowetting surface of passage 154 to the hydrophilic state is indicated in the lower view where the aqueous fluid takes on a relatively low contact angle 156. In this state the surface pressure asserted on the aqueous fluid 150 is smaller than hydraulic pressure resulting from force of gravity on the aqueous fluid 150. As such, the aqueous fluid can flow.

A valve mechanism as exemplified in FIG. 15 can be used at the outlets 105 through 109 of the reservoir device shown in FIG. 14. The outlets 105 through 109 can be configured to have a small enough diameter to assert sufficient surface tension on the aqueous liquid to prevent flow from the reservoirs 101 through 104 when the surface of the outlets 105 through 109 is in a hydrophobic state.

Throughout this application various publications, patents and published patent application have been referenced. The disclosures of these publications in their entireties are hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the claims below.

What is claimed is:

1. An apparatus for manipulating droplets comprising a substrate comprising an array of dynamic pads for performing droplet operations, wherein for at least a subset of the array of dynamic pads, each pad comprises a hydrophilic patch, wherein the ratio of the area of the hydrophilic patch to the dynamic pad allows the droplet to move from a first dynamic pad comprising the patch to a second dynamic pad, and wherein the dynamic pad is an electrowetting control pad comprising an electrode covered by a hydrophobic layer.

2. The apparatus of claim 1, wherein the size of the patch is smaller than the first dynamic pad.

3. The apparatus of claim 1, wherein the hydrophilic patch remains hydrophilic regardless of whether the first dynamic pad is in a hydrophilic or hydrophobic state.

4. The apparatus of claim 1, wherein the electrowetting control pad is the same size as the electrode.

5. The apparatus of claim 1, wherein the hydrophilic patch is on the same plane as the hydrophobic layer.

6. The apparatus of claim 1, wherein the first dynamic pad comprises a well comprising the hydrophilic patch.

7. The apparatus of claim 1, wherein the hydrophilic patch is comprised of one or more hydrophilic areas being separated from one another on the first dynamic pad.

8. The apparatus of claim 1, wherein the hydrophilic patch comprises a gel capable of indirect or direct nucleic acid molecule attachment.

9. The apparatus of claim 1, wherein the hydrophilic patch comprises one or more nucleic acids.

10. A method of moving a droplet, comprising the steps of:
(a) providing the apparatus of claim 1;
(b) moving a droplet on the substrate surface onto a first dynamic pad comprising a hydrophilic patch; and
(c) moving the droplet from the first dynamic pad to a second dynamic pad.

11. The method of claim 10, wherein the hydrophilic patch of step (b) comprises one or more primers.

12. The method of claim 11, wherein the droplet of step (b) comprises a plurality of nucleic acid molecules capable of hybridizing to the primers.

13. The method of claim 10, wherein the droplet of step (b) comprises one or more nucleic acid sequencing reagents.

14. The method of claim 10, wherein the droplet manipulation apparatus comprises a fill liquid that is immiscible to the droplet, and wherein the fill liquid flows past the droplet under a force that is independent of forces placed on the fluid by the droplet.

15. The method of claim 10, wherein the size of the hydrophilic patch is smaller than the first dynamic pad.

16. The method of claim 10, wherein the hydrophilic patch remains hydrophilic regardless of whether the electrowetting control pad is active.

17. The method of claim 10, wherein the electrowetting control pad is the same size as the electrode.

18. The method of claim 10, wherein the hydrophilic patch is on the same plane as the hydrophobic layer.

19. The method of claim 10, wherein the hydrophilic patch is comprised of one or more hydrophilic areas being separated from one another.

20. The method of claim 10, wherein the hydrophilic patch of step (b) comprises one or more nucleic acid molecules to be sequenced.

21. A method of sequencing a nucleic acid molecule, the method comprising the steps of:
(a) providing the apparatus of claim 1;
(b) transporting a droplet comprising one or more nucleic acid molecules to be sequenced to the hydrophilic patch;
(c) immobilizing the one or more nucleic acid molecules;
(d) sequencing the one or more nucleic acid molecules.

22. The method of claim 21, wherein the hydrophilic patch comprises one or more primers.

23. The method of claim 22, wherein step (c) includes hybridizing the nucleic acid molecules to the primers.

24. The method of claim 21, wherein prior to step (d) the nucleic acid molecules are amplified.

25. The method of claim 21, wherein the size of the patch is smaller than the first dynamic pad.

26. The method of claim 21, wherein the hydrophilic patch remains hydrophilic regardless of whether the electrowetting control pad is active.

27. The method of claim 21, wherein the electrowetting control pad is the same size as the electrode.

28. The method of claim 21, wherein the hydrophilic patch is on the same plane as the hydrophobic layer.

29. The method of claim 21, wherein the hydrophilic patch is comprised of one or more hydrophilic areas being separated from one another.

* * * * *